US012758557B2

(12) United States Patent
Bollong et al.

(10) Patent No.: US 12,758,557 B2

(45) Date of Patent: Oct. 13, 2026

(54) SMALL MOLECULE REGULATORS OF ALVEOLAR TYPE 2 CELL PROLIFERATION FOR THE TREATMENT OF PULMONARY DISEASES

(71) Applicant: THE SCRIPPS RESEARCH INSTITUTE, La Jolla, CA (US)

(72) Inventors: Michael J. Bollong, San Diego, CA (US); Peter G. Schultz, La Jolla, CA (US); Sida Shao, San Diego, CA (US); Arnab Chatterjee, San Diego, CA (US); Jian Jeffrey Chen, San Diego, CA (US); Nan Zhang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 467 days.

(21) Appl. No.: 18/261,467

(22) PCT Filed: Jan. 14, 2022

(86) PCT No.: PCT/US2022/070198

§ 371 (c)(1),
(2) Date: Jul. 13, 2023

(87) PCT Pub. No.: WO2022/155674

PCT Pub. Date: Jul. 21, 2022

(65) Prior Publication Data

US 2024/0115577 A1 Apr. 11, 2024

Related U.S. Application Data

(60) Provisional application No. 63/138,131, filed on Jan. 15, 2021.

(51) Int. Cl.

| | |
|---|---|
| ***A61K 31/522*** | (2006.01) |
| ***A61K 31/40*** | (2006.01) |
| ***A61K 31/403*** | (2006.01) |
| ***A61K 31/4162*** | (2006.01) |
| ***A61K 31/495*** | (2006.01) |
| ***A61K 31/496*** | (2006.01) |
| ***A61K 31/4985*** | (2006.01) |
| ***A61K 31/513*** | (2006.01) |
| ***A61K 31/519*** | (2006.01) |
| ***A61K 31/551*** | (2006.01) |
| ***A61K 31/69*** | (2006.01) |
| ***A61P 11/00*** | (2006.01) |

(52) U.S. Cl.

CPC ............ *A61K 31/522* (2013.01); *A61K 31/40* (2013.01); *A61K 31/403* (2013.01); *A61K 31/4162* (2013.01); *A61K 31/495* (2013.01); *A61K 31/496* (2013.01); *A61K 31/4985* (2013.01); *A61K 31/513* (2013.01); *A61K 31/519* (2013.01); *A61K 31/551* (2013.01); *A61K 31/69* (2013.01); *A61P 11/00* (2018.01)

(58) Field of Classification Search

CPC .. A61K 31/40; A61K 31/403; A61K 31/4162; A61K 31/495; A61K 31/496; A61K 31/4985; A61K 31/513; A61K 31/519; A61K 31/522; A61K 31/551; A61K 31/69; A61P 11/00

See application file for complete search history.

(56) References Cited

U.S. PATENT DOCUMENTS

| | | | |
|---|---|---|---|
| 9,416,196 | B2 | 8/2016 | Song et al. |
| 2010/0240611 | A1 | 9/2010 | Ronsheim et al. |

FOREIGN PATENT DOCUMENTS

| | | | |
|---|---|---|---|
| CN | 111116549 | A | 5/2020 |
| KR | 20200005355 | A | 1/2020 |
| WO | 2021005436 | A1 | 1/2021 |

OTHER PUBLICATIONS

Kawasaki, et al., "DPP4 inhibition by sitagliptin attenuates LPS-induced lung injury in mice", Am J Physiol Lung Cell Mol Physiol 315 (5), L834-L845 (2018).

Patent Cooperation Treaty, International Search Report and Written Opinion for PCT/US2022/070198, 19 pages, dated May 31, 2022.

Soare, et al., "Dipeptidylpeptidase 4 as a Marker of Activated Fibroblasts and a Potential Target for the Treatment of Fibrosis in Systemic Sclerosis", Arthritis Rheumatol 72 (1), 137-149 (2020).

Solerte, et al., "Dipeptidyl peptidase-4 (DPP4) inhibition in COVID-19", Acta Diabetol 57 (7), 779-783 (2020).

Xu, et al., "Dipeptidyl peptidase IV (DPP-4) inhibition alleviates pulmonary arterial remodeling in experimental pulmonary hypertension", Lab Invest 98 (10), 1333-1346 (2018).

Al Zoubi, et al., "Linagliptin Attenuates the Cardiac Dysfunction Associated With Experimental Sepsis in Mice With Pre-existing Type 2 Diabetes by Inhibiting NF-KB", Frontiers in Immunology 9, 2996, 1-13 (2018).

(Continued)

*Primary Examiner* — Sarah Pihonak

(74) *Attorney, Agent, or Firm* — Viksnins Harris Padys Malen LLP

(57) ABSTRACT

The present disclosure relates to compounds. and to their pharmaceutical compositions. that inhibit dipeptidyl peptidase IV (DPP4). Hie compounds selectively promote the proliferation of alveolar type 2 cells (AEC2s) and are useful in therapeutic methods of treating diseases whose etiology, for example, derives from epithelial degeneration and maladaptive remodeling, such as pulmonary' diseases like idiopathic pulmonary fibrosis (IFF), acute respiratory' distress syndrome (ARDS), and infant respiratory' distress syndromes (IRDS).

12 Claims, 11 Drawing Sheets

(56) References Cited

OTHER PUBLICATIONS

Guo, et al., "Dipeptidyl Peptidase-4 (DPP-4) Inhibitor Saxagliptin Alleviates Lipopolysaccharide-Induced Acute Lung Injury via Regulating the Nrf-2/HO-1 and NF- $_{\kappa}$B Pathways", Journal of Investigative Surgery 34(7), 695-702 (2021).

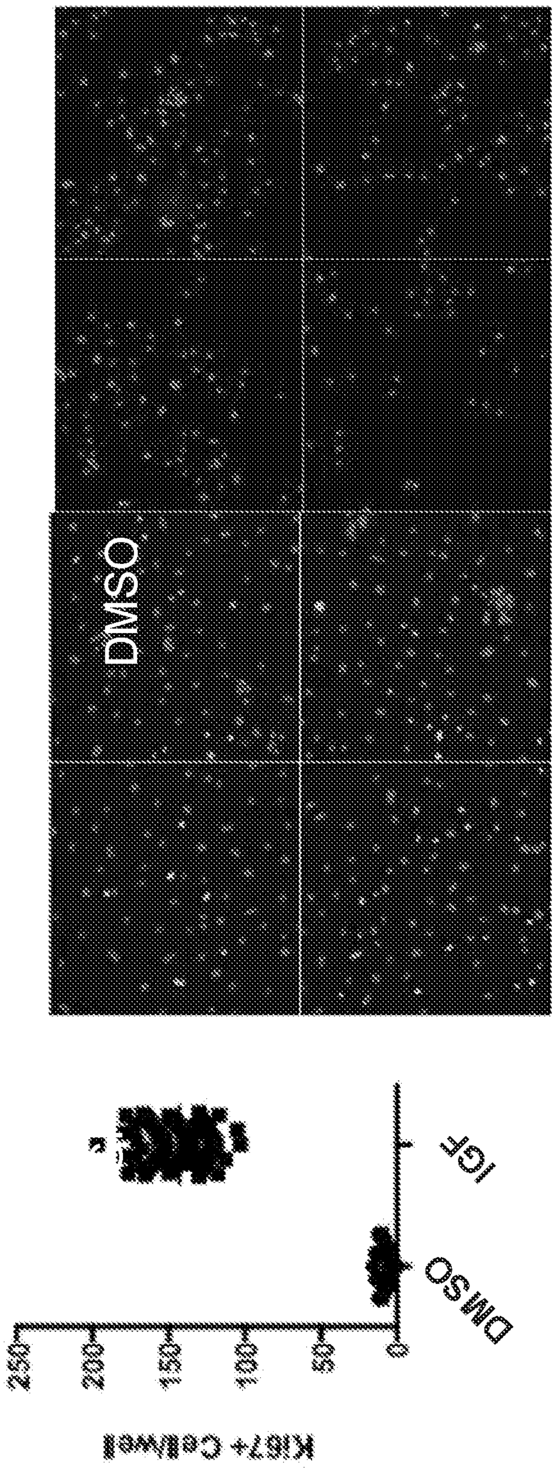
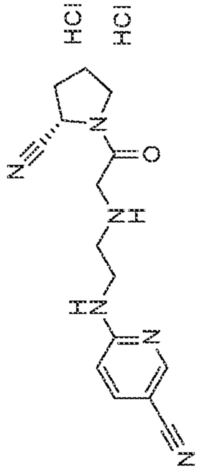
NVP-728
FIG. 1A

FIG. 3

| Compound | S1PR Subtype | Reported EC50 | Active? | $EC_{50}$ AEC2 proliferation | Relative proliferative efficacy (Precent of IGF) | Toxicity |
|---|---|---|---|---|---|---|
| Siponimod | $S1PR_{1\&5}$ Agonist | $S1PR_{1\&5}$ <1nM | Yes | 50nM~200nM* | 41.7% | Toxic above 5uM |
| FTY-720 | $S1PR_{1,3,4\&5}$ Agonist | All sub nM | Yes | ~600nM | 28.8% | Not toxic at 20uM |
| Ozanimod | $S1PR_{1\&5}$ Agonist | S1PR1=0.41nM S1PR5=11nM | Yes | 60nM~100nM in all reps | Inconclusive | N/A |
| CYM-5442 | $S1PR_1$ Agonist | S1PR1=1nM | Yes | 250~400nM | 35.2% | N/A |
| SEW-2871 | $S1PR_1$ Agonist | S1PR1=1nM | Yes | N/D Active at 100 nM | Inconclusive | N/A |
| CYM-5520 | $S1PR_2$ Agonist | S1PR2=0.5nM | No | Inactive | Inactive | N/A |
| CYM-5541 | $S1PR_3$ Agonist | S1PR3=~100nM | No | Inactive | Inactive | N/A |
| CYM-50260 | $S1PR_4$ Agonist | S1PR4=45nM | No | Inactive | Inactive | N/A |
| A-971432 | $S1PR_5$ Agonist | S1PR1=300nM S1PR5=5nM | Inconclusive | Not Conclusive | Inconclusive | N/A |

SMALL MOLECULE REGULATORS OF ALVEOLAR TYPE 2 CELL PROLIFERATION FOR THE TREATMENT OF PULMONARY DISEASES

BACKGROUND

Pharmacological stimulation of lower airway repair has significant potential for treating a variety of conditions in which alveolar destruction and maladaptive remodeling are causative of disease. The alveolus, the primary unit of mammalian gas exchange, is composed of two epithelial cell types: large squamous alveolar type 1 cells (AEC1s), which provide surface area for gas exchange, and cuboidal alveolar type 2 cells (AEC2s), which secrete surfactant.[1] In addition, AEC2s have been identified as the primary progenitor cell type responsible for repopulating the alveolar epithelium.[2] AEC2s clonally proliferate over adulthood, asymmetrically dividing to give rise to AEC1s and AEC2s.[2] It has been additionally demonstrated that idiopathic pulmonary fibrosis (IPF) is caused by exhaustion of the stem cell capacity of AEC2s.[3] Diminished AEC2 proliferation results in denuded alveolar basement membranes, which ultimately promotes colonization of the lower airway by hyperplastic upper airway-derived epithelial cells and extracellular matrix-secreting myofibroblasts.[3] Additionally, it has been demonstrated that restoring AEC2 proliferation through treatment with exogenous factors (IL-6 or hyaluronic acid) inhibits disease severity in mouse models of IPF.[4] In addition to IPF, acute respiratory distress syndrome (ARDS)—the acute loss of alveolar epithelial barrier function—is caused by damage to and insufficient reparative growth by AEC2 cells.[5]

SUMMARY

The present disclosure provides, in various embodiments, a compound that is useful. for example, in promoting specific proliferation of AEC2s relative to other cell types in the lung. Thus, in various embodiments, the present disclosure provides a method for selectively increasing the proliferation of cuboidal alveolar type 2 (AEC2) cells in a subject in need thereof, or for restoring diminished proliferation of AEC2 cells in a subject in need thereof. The method comprises administering to the subject a dipeptidyl peptidase-4 (DPP4) inhibitor, or a pharmaceutically acceptable salt thereof, as described in the present disclosure.

In additional embodiments, the present disclosure provides a method for treating a disease in a subject suffering therefrom, wherein the disease etiology derives from epithelial degeneration and/or maladaptive remodeling. The method comprises administering to the subject a dipeptidyl peptidase-4 (DPP4) inhibitor, or a pharmaceutically acceptable salt thereof, as described in the present disclosure.

In another embodiment, the present disclosure provides a method for treating a pulmonary disease or lung condition in a subject suffering therefrom. The method comprises pulmonary administration to the subject a dipeptidyl peptidase-4 (DPP4) inhibitor or a pharmaceutically acceptable salt thereof.

BRIEF DESCRIPTION OF THE DRAWINGS

FIG. 1A-FIG. 1C. A high content imaging screen identifies DPP4 inhibitors and S1P1R modulators as small molecule proliferators of AEC2 cells. FIG. 1A: Quantification and representative images of the percentage of Ki67 AEC2s in response to insulin-like growth factor 1 (IGF1) treatment, a mitogenic positive control. Chemical structures. quantification of AEC2 cell percentage Ki67 positivity, and percent pulmonary fibroblast activation of the confirmed screening hits NVP-728 (FIG. 1B) and siponimod (FIG. 1C).

FIG. 2A: Pharmacological or genetic attenuation of DPP4 activity promotes AEC2 expansion by an IGF1-driven autocrine feed-forward loop. FIG. 2B: Ki67 positive AEC2s per well are treated with the indicated concentrations of DPP4 inhibitors (Ki67 positive (left) and total AEC2 numbers (right) in response to siRNA-mediated knockdown of DPP4. FIG. 2C: Ki67 positive AEC2s per well treated with the indicated concentrations of IGF in combination with DPP4 inhibitors. FIG. 2D: Representative images of Crystal-violet stained AEC2 monoloayer cultures in response to combination treatment with exogenous IGF and soluble DPP4.

FIG. 3. Activity of the indicated S1P receptor subtype modulators in assays for AEC2 proliferation and toxicity.

FIG. 7A: Linagliptin induces phospholipidosis in vitro. FIG. 7B: Linagliptin displays a narrow efficacious dosing range in mouse acute lung injury (ALI) models.

DETAILED DESCRIPTION

Figure 1B:
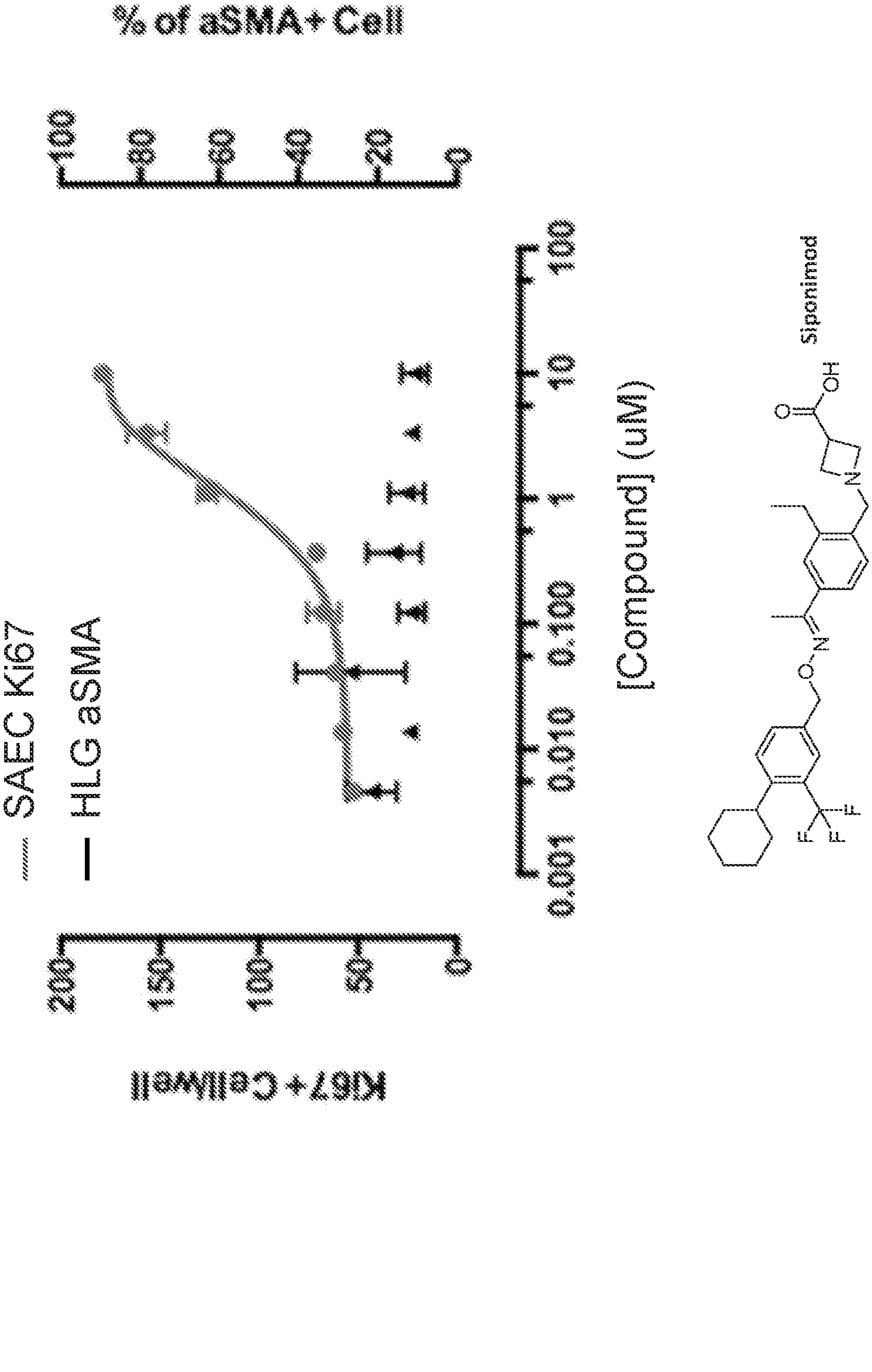

The present disclosure satisfies a long-felt need for drug-like compounds that stimulate reparative proliferation of pulmonary stem- and progenitor-cell populations. Compounds of the present disclosure promote specific proliferation of AEC2s relative to other cell types in the lung (e.g., pulmonary fibroblasts) and thereby exhibit disease-modifying efficacy in a number of lower airway diseases. Furthermore, the compounds are useful as inhibitors of dipeptidyl peptidase IV (DPP4).

Definitions

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure. including tautomeric forms of the compound. The compounds of the present disclosure may also exist in open-chain or cyclized forms. In some cases. one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers. diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, and/or tautomer thereof. Thus, for instance, a compound of the present disclosure includes a pharmaceutically acceptable salt of a tautomer of the compound.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this example, the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

"Inhibitor" means a compound which prevents or reduces the expression, catalytic activity, and/or localization (i.e., local concentration) of DPP4.

Methods of Use

The present disclosure is premised, in part, upon the surprising discovery that DPP4 inhibition results in expansion of alveolar type 2 cells (AEC2s), an effect that is harnessed for use in regenerative repair in lung injury and fibrosis. among other diseases and conditions. Because DPP4 inhibitors disclosed herein are typically safe and effective for labeled uses, as established by the U.S. FDA, the present disclosure is further premised upon the direct repurposing of gliptins for use in treating these diseases and conditions, such as pulmonary and other diseases. As described herein and illustrated throughout the examples, pharmacokinetic and efficacy data from the mouse established that oral doses of the compounds for their labeled uses surprisingly would require multiplication by about 10-fold to exhibit efficacy in human patients.

Based upon these and other discoveries, the present disclosure provides in various embodiments a method for selectively increasing the proliferation of cuboidal alveolar type 2 (AEC2) cells in a subject in need thereof, or for restoring diminished proliferation of AEC2 cells in a subject in need thereof. The method comprises administering to the subject a dipeptidyl peptidase-4 (DPP4) inhibitor or a pharmaceutically acceptable salt thereof.

In additional embodiments, the present disclosure provides a method for treating a disease in a subject suffering therefrom, wherein the disease etiology derives from epithelial degeneration and/or maladaptive remodeling. The method comprises administering to the subject a dipeptidyl peptidase-4 (DPP4) inhibitor or a pharmaceutically acceptable salt thereof.

In various embodiments, the disease is a pulmonary disease or lung condition. Illustrative embodiments include those wherein the disease is selected from Idiopathic pulmonary fibrosis (IPF), Acute respiratory distress syndrome (ARDS), Chronic Obstructive Pulmonary Disease (COPD), Emphysema, Silicosis, Asbestosis, Pneumoconiosis, Aluminosis, Bauxite fibrosis, Berylliosis, Siderosis, Stannosis, Pulmonary Talcosis, Labrador lung (mixed dust Pneumoconiosis), Sarcoidosis, Hypersensitivity pneumonitis (HP)/extrinsic allergic alveolitis (EAA), Chronic Bronchitis, Desquamative interstitial pneumonia (DIP), Respiratory bronchiolitis interstitial lung disease (RBILD), Acute interstitial pneumonia (AIP), Nonspecific interstitial pneumonia (NSIP), Cryptogenic organizing pneumonia (COP=idiopathic BOOP), Secondary organizing pneumonia (BOOP), Lymphoid interstitial pneumonia (LIP), Idiopathic interstitial pneumonia: unspecified, Hypereosinophilic lung diseases, Tuberculosis (TB), Pulmonary Edema, Interstitial Lung Disease, Bronchopulmonary Dysplasia (BPD), Coronavirus, COVID-19, Cryptogenic Organizing Pneumonia (COP), Cystic Fibrosis (CF), E-cigarette or Vaping Use-Associated Lung Injury (EVALI), Hantavirus Pulmonary Syndrome (HPS), Histoplasmosis, Influenza, Legionnaires Disease, MAC Lung Disease, Alpha-1 Antitrypsin Deficiency, Aspergillosis, Lymphangiolciomyomatosis (LAM), Middle Eastern Respiratory Syndrome (MERS), Nontuberculous Mycobacterial Lung Disease (NTM), Lung cancer, Pulmonary Embolism, Goodpasture syndrome, idiopathic pulmonary hemosiderosis, alveolar hemorrhage syndrome of undetermined origin, alveolar hemorrhage syndrome of determined origin, Sporadic pulmonary lymphangioleiomyomatosis (S-LAM), Pulmonary lymphangioleiomyomatosis in tuberous sclerosis (TSC-LAM), Alveolar proteinosis, Pulmonary amyloidosis, Primary pulmonary lymphoma, Primary ciliary dyskinesia (without or with situs inversus), Rare cause of hypersensitivity pneumonitis (all causes other than farmer's lung disease and pigeon breeder's lung disease), Pulmonary arteriovenous malformations in hereditary hemorrhagic telangiectasia (HHT), interstitial lung disease in systemic sclerosis, interstitial lung disease in rheumatoid arthritis, interstitial lung disease in idiopathic inflammatory myopathies (polymyositis, dermatomyositis, anti-synthetase syndrome), interstitial lung disease in Sjögren syndrome, interstitial lung disease in mixed connective tissue disease (MCTD), interstitial lung disease in overlap syndromes, interstitial lung disease in undifferentiated connective tissue disease, and Bronchiolitis obliterans (in non-transplanted patients).

In additional embodiments, the disease is an inflammatory disease or disorder. Examples include, without limitation, a disease selected from Infectious colitis, Ulcerative colitis, Crohn's disease, Ischemic colitis, Radiation colitis, Peptic ulcer, Intestinal cancer, Intestinal obstruction, Rheumatoid arthritis, Psoriatic arthritis, Hashimoto thyroiditis, Systemic lupus erythematosus, Multiple Sclerosis, Graves' Disease, Type 1 Diabetes Mellitus, Psoriasis, Ankylosing spondylitis, Scleroderma, Myositis, Gout, Antiphospholipid Antibody Syndrome (APS), Vasculitis, Dilated cardiomyopathy, Hypertrophic cardiomyopathy, Restrictive cardiomyopathy, Left-sided heart failure, Right-sided heart failure, Systolic heart failure, Diastolic heart failure (heart failure with preserved ejection fraction), Atrial Septal Defect, Atrioventricular Septal Defect, Coarctation of the Aorta, Double-outlet Right Ventricle, d-Transposition of the Great Arteries, Ebstein Anomaly, Hypoplastic Left Heart Syndrome, Interrupted Aortic Arch, Pulmonary Atresia, Single Ventricle, Tetralogy of Fallot, Total Anomalous Pulmonary Venous Return, Tricuspid Atresia, Truncus Arteriosus, Ventricular Septal Defect, Polycystic kidney disease, Diabetes Insipidus, Goodpasture's Disease, IgA Vasculitis, IgA Nephropathy, Lupus Nephritis, Adult Nephrotic Syndrome, Childhood Nephrotic Syndrome, Hemolytic Uremic Syndrome, Medullary Sponge Kidney, Kidney dysplasia, Renal artery stenosis, Renovascular hypertension, Renal tubular acidosis, Alport syndrome, Wenger's granulomatosis, Alagille syndrome, Cystinosis, Fabry disease, Focal segmental glomerulosclerosis (FSGS), Glomerulonephritis, aHUS (atypical hemolytic uremic syndrome), Hemolytic uremic syndrome (HUS), Henoch-Schönlein purpura, IgA nephropathy (Berger's disease), Interstitial nephritis, Minimal change disease, Nephrotic syndrome, Thrombotic thrombocytopenia purpura (TTP), Granulomatosis with polyangiitis (GPA), Eczema, Psoriasis, Cellulitis, Impetigo, Atopic dermatitis, Epidermolysis Bullosa, Lichen Sclerosis, Ichthyosis, Vitiligo, Acral peeling skin syndrome, Blau syndrome, Primary cutaneous amyloidosis, Cutaneous abscess, Pressure Ulcers, Blepharitis, Furunculosis, Full or partial thickness burns, Capillaritis, Cellulitis, Corneal Abrasion, Corneal Erosion, Xerosis, Lichen Planus, Lichen Simplex Chronicus, Venous Ulcer (Stasis Ulcer), Adult Still's disease, Agammaglobulinemia, Alopecia areata, Autoimmune angioedema, Autoimmune dysautonomia, Autoimmune encephalomyelitis, Autoimmune hepatitis, Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Bullous pemphigoid, Celiac disease, Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Coxsackie myocarditis, CREST syndrome, Dermatitis herpetiformis, Dermatomyositis, Devic's disease (neuromyelitis optica), Discoid lupus, Eosinophilic esophagitis (EoE), Eosinophilic fasciitis, Erythema nodosum, Essential mixed cryoglobulinemia, Giant cell arteritis (temporal arteritis), Giant cell myocarditis, Granulomatosis with Polyangiitis, Guillain-Barre syndrome, Hashimoto's thyroiditis, Henoch-Schonlein purpura (HSP), Herpes gestationis or pemphigoid gestationis (PG), Hypogammalglobulinemia, IgG4-related sclerosing disease, Immune thrombocytopenia purpura (ITP), Inclusion body myositis (IBM), Lambert-Eaton syndrome, Leukocytoclastic vasculitis, Linear IgA disease (LAD), Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Primary biliary cirrhosis, Primary sclerosing cholangitis, Progesterone dermatitis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenia purpura (TTP), Thyroid eye disease (TED), Alagille Syndrome, Alcohol-Related Liver Disease, Autoimmune Hepatitis, Biliary Atresia, Cirrhosis, Lysosomal Acid Lipase Deficiency (LAL-D), Liver Cysts, Liver Cancer, Newborn Jaundice, Non-Alcoholic Fatty Liver Disease, Non-Alcoholic Steatohepatitis, Primary Biliary Cholangitis (PBC), Progressive Familial Intrahepatic Cholestasis (PFIC), Osteoporosis, Paget's Disease, Osteonecrosis, Osteoarthritis, Low Bone Density, Gout, Fibrous Dysplasia, Marfan Syndrome, and Osteogenesis Imperfecta.

In various embodiments, the DPP4 inhibitor or pharmaceutically acceptable salt thereof is one selected from Table 1 below.

TABLE 1

Exemplary DPP4 Inhibitors

| Cpd # | Chemical structure | Name |
|---|---|---|
| 1 | 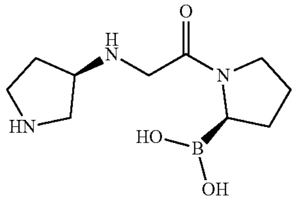 [SMILES: O=C(CN[C@@H]1CCNC1)N1CCC[C@H]1B(O)O] | ((R)-1-(((R)-pyrrolidin-3-yl)glycyl)pyrrolidin-2-yl)boronic acid (Dutogliptin) |
| 2 | 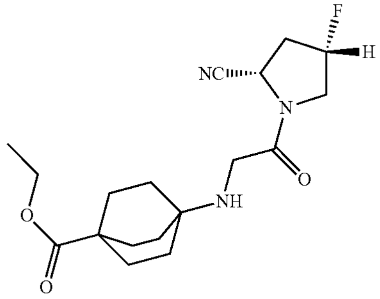 [SMILES: CCOC(=O)C12CCC(NCC(=O)N3C[C@@H](F)C[C@H]3C#N)(CC1)CC2] | ethyl 4-((2-((2S,4S)-2-cyano-4-fluoropyrrolidin-1-yl)-2-oxoethyl)amino)bicyclo[2.2.2]octane-1-carboxylate (Bisegliptin) |
| 3 | 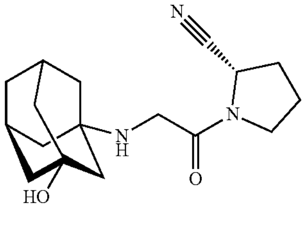 | (2S)-1-(((1S,3R,5S)-3-hydroxyadamantan-1-yl)glycyl)pyrrolidine-2-carbonitrile (vildagliptin) |
| 4 | 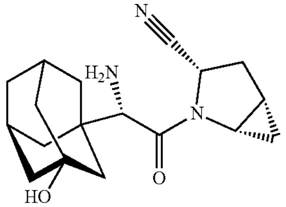 | (1S,3S,5S)-2-((2S)-2-amino-2-((1S,3R,5S)-3-hydroxyadamantan-1-yl)acetyl)-2-azabicyclo[3.1.0]hexane-3-carbonitrile (saxaglitptin) |

TABLE 1-continued

Exemplary DPP4 Inhibitors

| Cpd # | Chemical structure | Name |
|---|---|---|
| 5 | 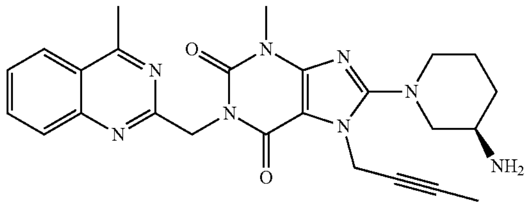 [SMILES: CC#CCn1c(N2CCC[C@@H](N)C2)nc2c1c(=O)n(Cc1nc(C)c3ccccc3n1)c(=O)n2C] | (R)-8-(3-aminopiperidin-1-yl)-7-(but-2-yn-1-yl)-3-methyl-1-((4-methylquinazolin-2-yl)methyl)-3,7-dihydro-1H-purine-2,6-dione (linagliptin) |
| 6 | 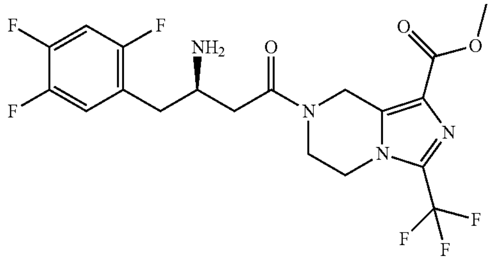 [SMILES: COC(=O)c1nc(C(F)(F)F)n2c1CN(C(=O)C[C@H](N)Cc1cc(F)c(F)cc1F)CC2] | methyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (Retagliptin) |
| 7 | 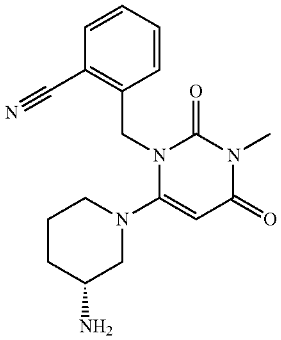 [SMILES: Cn1c(=O)cc(N2CCC[C@@H](N)C2)n(Cc2ccccc2C#N)c1=O] | (R)-2-((6-(3-aminopiperidin-1-yl)-3-methyl-2,4-dioxo-3,4-dihydropyrimidin-1(2H)-yl)methyl)benzonitrile (alogliptin) |
| 8 | 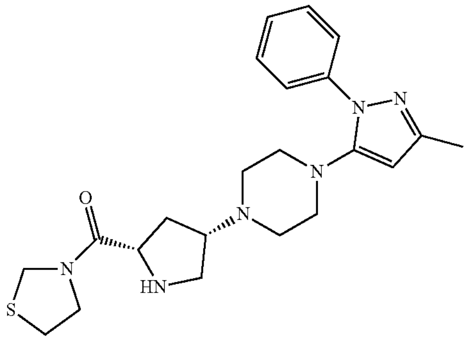 [SMILES: Cc1cc(N2CCN([C@@H]3CN[C@H](C(=O)N4CCSC4)C3)CC2)n(-c2ccccc2)n1] | ((2S,4S)-4-(4-(3-methyl-1-phenyl-1H-pyrazol-5-yl)piperazin-1-yl)pyrrolidin-2-yl)(thiazolidin-3-yl)methanone (Teneligliptin) |
| 9 | 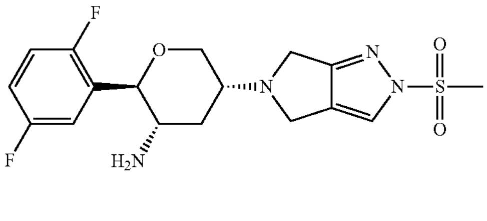 [SMILES: CS(=O)(=O)n1cc2c(n1)CN([C@H]1CO[C@H](c3cc(F)ccc3F)[C@@H](N)C1)C2] | (2R,3S,5R)-2-(2,5-difluorophenyl)-5-(2-(methylsulfonyl)-2,6-dihydropyrrolo[3,4-c]pyrazol-5(4H)-yl)tetrahydro-2H-pyran-3-amine (omarigliptin) |

TABLE 1-continued

| Exemplary DPP4 Inhibitors | | |
|---|---|---|
| Cpd # | Chemical structure | Name |
| 10 | 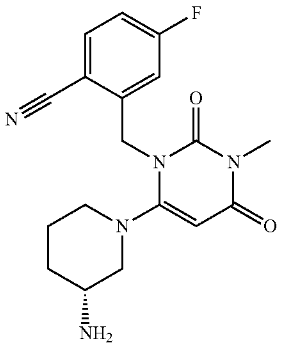 [SMILES: Cn1c(=O)cc(N2CCC[C@@H](N)C2)n(Cc2cc(F)ccc2C#N)c1=O] | (R)-2-((6-(3-aminopiperidin-1-yl)-3-methyl-2,4-dioxo-3,4-dihydropyrimidin-1(2H)-yl)methyl)-4-fluorobenzonitrile (Trelagliptin) |
| 11 | 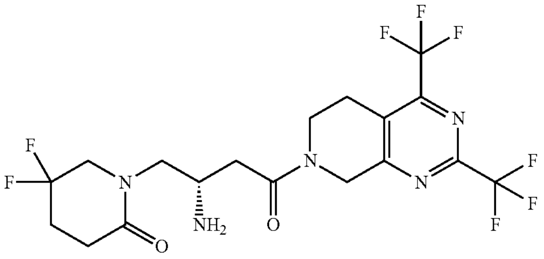 [SMILES: N[C@@H](CC(=O)N1CCc2c(nc(C(F)(F)F)nc2C(F)(F)F)C1)CN1CC(F)(F)CCC1=O] | (S)-1-(2-amino-4-(2,4-bis(trifluoromethyl)-5,8-dihydropyrido[3,4-d]pyrimidin-7(6H)-yl)-4-oxobutyl)-5,5-difluoropiperidin-2-one (Gemigliptin) |
| 12 | 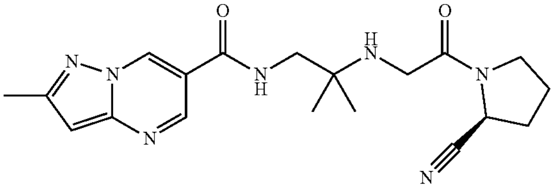 [SMILES: Cc1cc2ncc(C(=O)NCC(C)(C)NCC(=O)N3CCC[C@H]3C#N)cn2n1] | (S)-N-(2-((2-(2-cyanopyrrolidin-1-yl)-2-oxoethyl)amino)-2-methylpropyl)-2-methylpyrazolo[1,5-a]pyrimidine-6-carboxamide (Anagliptin) |
| 13 | 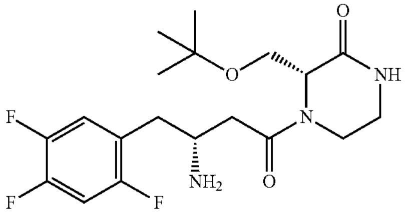 [SMILES: CC(C)(C)OC[C@@H]1C(=O)NCCN1C(=O)C[C@H](N)Cc1cc(F)c(F)cc1F] | (R)-4-((R)-3-amino-4-(2,4,5-trifluorophenyl)butanoyl)-3-(tert-butoxymethyl)piperazin-2-one (evogliptin) |
| 14 | 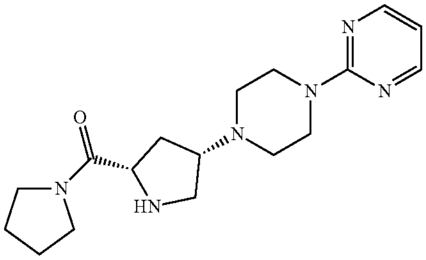 [SMILES: O=C([C@@H]1C[C@H](N2CCN(c3ncccn3)CC2)CN1)N1CCCC1] | ((2S,4S)-4-(4-(pyrimidin-2-yl)piperazin-1-yl)pyrrolidin-2-yl)(pyrrolidin-1-yl)methanone (gosogliptin) |

In still additional embodiments, the DPP4 inhibitor or pharmaceutically acceptable salt thereof is one selected from Table 2 below.

TABLE 2

| Exemplary DPP4 Inhibitors | |
|---|---|
| Structure | Name |
| 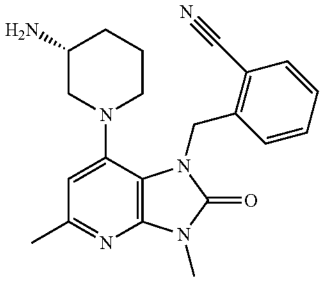 2 HCl | (R)-2-((7-(3-aminopiperidin-1-yl)-3,5-dimethyl-2-oxo-2,3-dihydro-1H-imidazo[4,5-b]pyridin-1-yl)methyl)benzonitrile dichloride (Imigliptin dihydrochloride) |
| 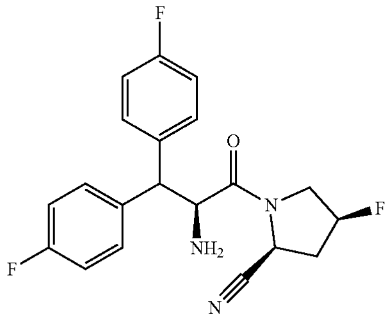 [SMILES: N#C[C@@H]1C[C@H](F)CN1C(=O)[C@@H](N)C(c1ccc(F)cc1)c1ccc(F)cc1] | (2S,4S)-1-((S)-2-amino-3,3-bis(4-fluorophenyl)propanoyl)-4-fluoropyrrolidine-2-carbonitrile (Denagliptin) |
| 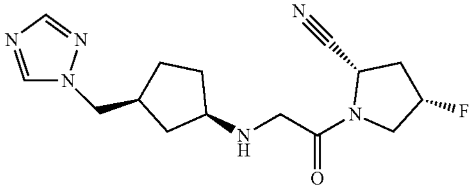 [SMILES: N#C[C@@H]1C[C@H](F)CN1C(=O)CN[C@@H]1CC[C@H](Cn2cncn2)C1] | (2S,4S)-1-(((1R,3S)-3-((1H-1,2,4-triazol-1-yl)methyl)cyclopentyl)glycyl)-4-fluoropyrrolidine-2-carbonitrile (Melogliptin) |
| 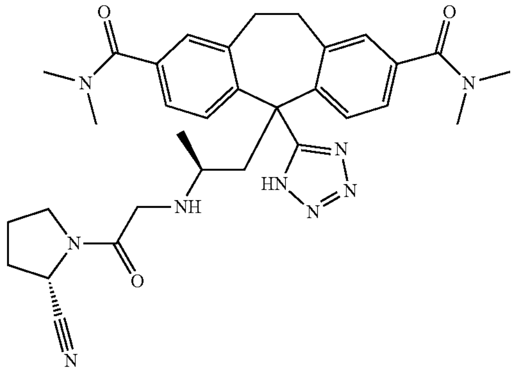 [SMILES: C[C@@H](CC1(c2nnn[nH]2)c2ccc(C(=O)N(C)C)cc2CCc2cc(C(=O)N(C)C)ccc21)NCC(=O)N1CCC[C@H]1C#N] | 5-((S)-2-((2-((S)-2-cyanopyrrolidin-1-yl)-2-oxoethyl)amino)propyl)-N2,N2,N8,N8-tetramethyl-5-(1H-tetrazol-5-yl)-10,11-dihydro-5H-dibenzo[a,d][7]annulene-2,8-dicarboxamide (AMG-222) |
| 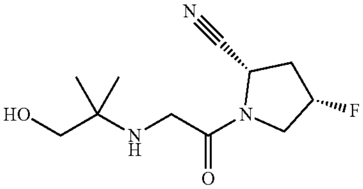 [SMILES: CC(C)(CO)NCC(=O)N1C[C@@H](F)C[C@H]1C#N] | (2S,4S)-4-fluoro-1-((1-hydroxy-2-methylpropan-2-yl)glycyl)pyrrolidine-2-carbonitrile (TS-021) |

TABLE 2-continued

| Exemplary DPP4 Inhibitors | |
|---|---|
| Structure | Name |
| 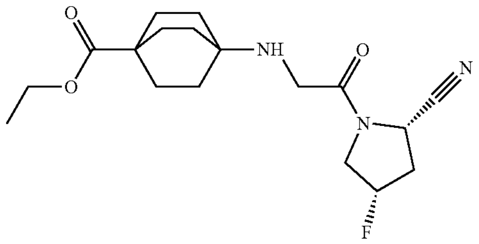 [SMILES: CCOC(=O)C12CCC(NCC(=O)N3C[C@@H](F)C[C@H]3C#N)(CC1)CC2] | ethyl 4-((2-((2S,4S)-2-cyano-4-fluoropyrrolidin-1-yl)-2-oxoethyl)amino)bicyclo[2.2.2]octane-1-carboxylate (KRP-104) |
| 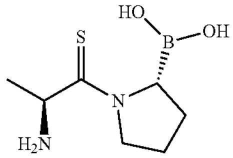 | ((R)-1-((S)-2-aminopropanethioyl)pyrrolidin-2-yl)boronic acid (ARI-2243) |
| 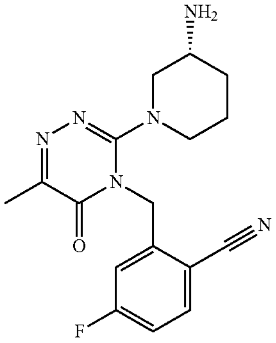 [SMILES: Cc1nnc(N2CCC[C@@H](N)C2)n(Cc2cc(F)ccc2C#N)c1=O] | (R)-2-((3-(3-aminopiperidin-1-yl)-6-methyl-5-oxo-1,2,4-triazin-4(5H)-yl)methyl)-4-fluorobenzonitrile (Fotagliptin) |
| 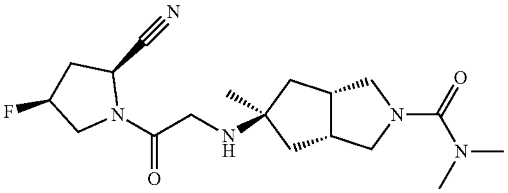 [SMILES: CN(C)C(=O)N1C[C@@H]2C[C@@](C)(NCC(=O)N3C[C@@H](F)C[C@H]3C#N)C[C@@H]2C1] | (3aR,5s,6aS)-5-((2-((2S,4S)-2-cyano-4-fluoropyrrolidin-1-yl)-2-oxoethyl)amino)-N,N,5-trimethylhexahydrocyclopenta[c]pyrrole-2(1H)-carboxamide (SHR-117887) |
| 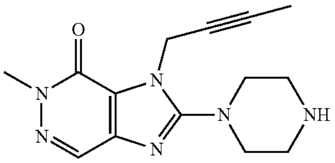 [SMILES: CC#CCn1c(N2CCNCC2)nc2cnn(C)c(=O)c21] | 3-(but-2-yn-1-yl)-5-methyl-2-(piperazin-1-yl)-3,5-dihydro-4H-imidazo[4,5-d]pyridazin-4-one (E-3024) |
| 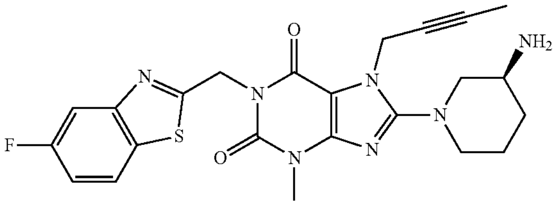 [SMILES: CC#CCn1c(N2CCC[C@H](N)C2)nc2c1c(=O)n(Cc1nc3cc(F)ccc3s1)c(=O)n2C] | (S)-8-(3-aminopiperidin-1-yl)-7-(but-2-yn-1-yl)-1-((5-fluorobenzo[d]thiazol-2-yl)methyl)-3-methyl-3,7-dihydro-1H-purine-2,6-dione (Yogliptin) |

TABLE 2-continued

| Exemplary DPP4 Inhibitors | |
|---|---|
| Structure | Name |
| 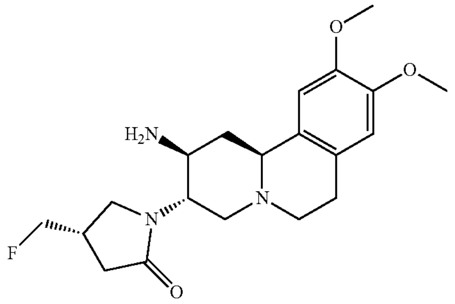 [SMILES: COc1cc2c(cc1OC)[C@@H]1C[C@H](N)[C@@H](N3C[C@@H](CF)CC3=O)CN1CC2] | (S)-1-((2S,3S,11bS)-2-amino-9,10-dimethoxy-1,3,4,6,7,11b-hexahydro-2H-pyrido[2,1-a]isoquinolin-3-yl)-4-(fluoromethyl)pyrrolidin-2-one (DPP-728/carmegliptin)) |
| 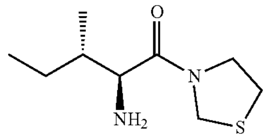 | (2S,3S)-2-amino-3-methyl-1-(thiazolidin-3-yl)pentan-1-one (P32/98) |
| | PSN-9301 |
| 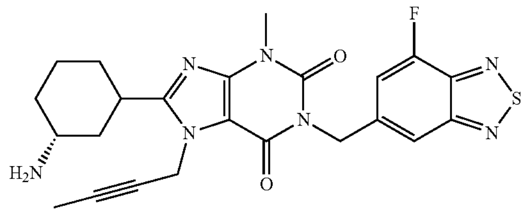 [SMILES: CC#CCn1c(C2CCC[C@@H](N)C2)nc2c1c(=O)n(Cc1cc(F)c3nsnc3c1)c(=O)n2C] | TQ-F3083 |
| 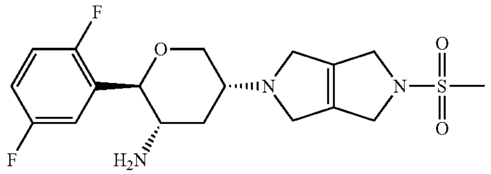 [SMILES: CS(=O)(=O)N1CC2=C(CN([C@H]3CO[C@H](c4cc(F)ccc4F)[C@@H](N)C3)C2)C1] | (2R,3S,5R)-2-(2,5-difluorophenyl)-5-(5-(methylsulfonyl)-3,4,5,6-tetrahydropyrrolo[3,4-c]pyrrol-2(1H)-yl)tetrahydro-2H-pyran-3-amine (ZYDPLA-1) |
| | DSP-7238 |
| 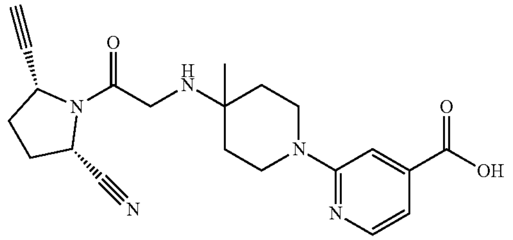 [SMILES: C#C[C@H]1CC[C@@H](C#N)N1C(=O)CNC1(C)CCN(c2cc(C(=O)O)ccn2)CC1] | 2-(4-((2-((2S,5R)-2-cyano-5-ethynylpyrrolidin-1-yl)-2-oxoethyl)amino)-4-methylpiperidin-1-yl)isonicotinic acid (ABT-279) |
| 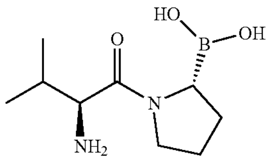 | ((R)-1-(L-valyl)pyrrolidin-2-yl)boronic acid (BXCL-701/talabostat)) |

In additional embodiments, the DPP4 inhibitor or pharmaceutically acceptable salt thereof is one selected from Table 3 below.

TABLE 3

Exemplary DPP4 Inhibitors or their prodrugs

| Cpd # | Chemical structure | Name |
| --- | --- | --- |
| 15 | 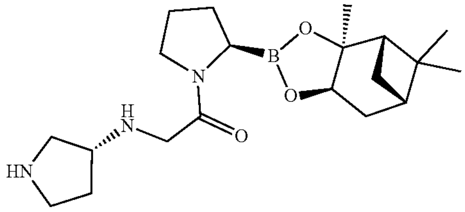 [SMILES: CC1(C)[C@@H]2C[C@H]3OB([C@@H]4CCCN4C(=O)CN[C@@H]4CCNC4)O[C@@]3(C)[C@H]1C2] | 2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl)ethan-1-one |
| 16 | 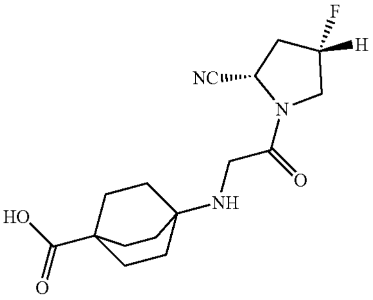 [SMILES: N#C[C@@H]1C[C@H](F)CN1C(=O)CNC12CCC(C(=O)O)(CC1)CC2] | 4-((2-((2S,4S)-2-cyano-4-fluoropyrrolidin-1-yl)-2-oxoethyl)amino)bicyclo[2.2.2]octane-1-carboxylic acid |
| 17 | 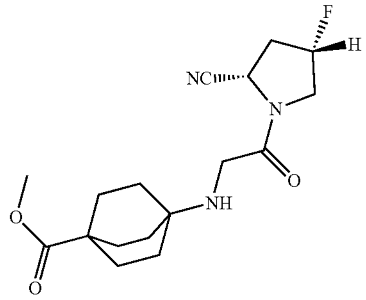 [SMILES: COC(=O)C12CCC(NCC(=O)N3C[C@@H](F)C[C@H]3C#N)(CC1)CC2] | methyl 4-((2-((2S,4S)-2-cyano-4-fluoropyrrolidin-1-yl)-2-oxoethyl)amino)bicyclo[2.2.2]octane-1-carboxylate |
| 18 | 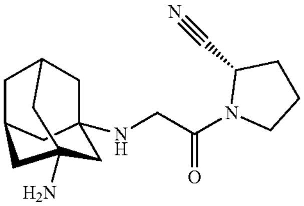 | (2S)-1-(((1S,3R,5R)-3-aminoadamantan-1-yl)glycyl)pyrrolidine-2-carbonitrile |
| 19 | 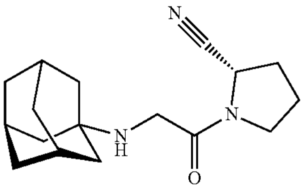 | (2S)-1-(((1r,3R,5S)-adamantan-1-yl)glycyl)pyrrolidine-2-carbonitrile |
| 20 | 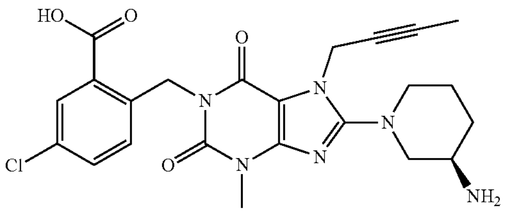 [SMILES: CC#CCn1c(N2CCC[C@@H](N)C2)nc2c1c(=O)n(Cc1ccc(Cl)cc1C(=O)O)c(=O)n2C] | (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoic acid |

TABLE 3-continued

| Cpd # | Chemical structure | Name |
|---|---|---|
| | Exemplary DPP4 Inhibitors or their prodrugs | |
| 21 | 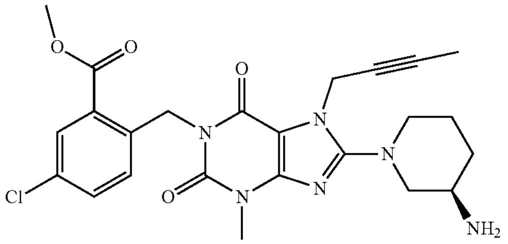 [SMILES: CC#CCn1c(N2CCC[C@@H](N)C2)nc2c1c(=O)n(Cc1ccc(Cl)cc1C(=O)OC)c(=O)n2C] | methyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate |
| 22 | 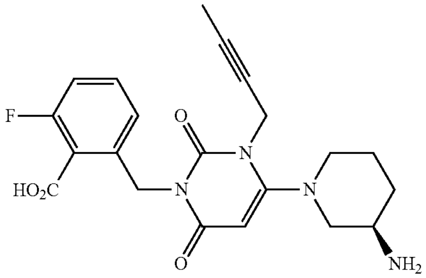 [SMILES: CC#CCn1c(N2CCC[C@@H](N)C2)cc(=O)n(Cc2cccc(F)c2C(=O)O)c1=O] | (R)-2-((4-(3-aminopiperidin-1-yl)-3-(but-2-yn-1-yl)-2,6-dioxo-3,6-dihydropyrimidin-1(2H)-yl)methyl)-6-fluorobenzoic acid |
| 23 | 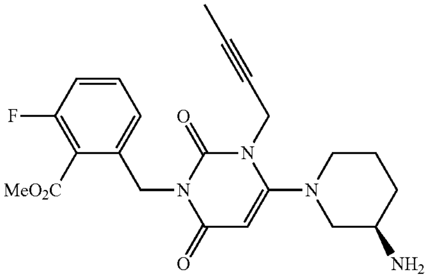 [SMILES: CC#CCn1c(N2CCC[C@@H](N)C2)cc(=O)n(Cc2cccc(F)c2C(=O)OC)c1=O] | methyl (R)-2-((4-(3-aminopiperidin-1-yl)-3-(but-2-yn-1-yl)-2,6-dioxo-3,6-dihydropyrimidin-1(2H)-yl)methyl)-6-fluorobenzoate |
| 24 | 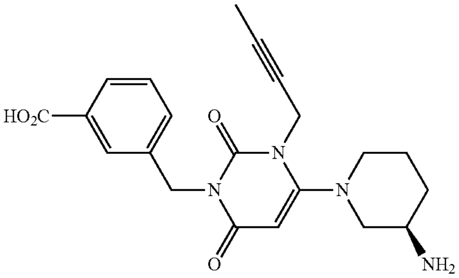 [SMILES: CC#CCn1c(N2CCC[C@@H](N)C2)cc(=O)n(Cc2cccc(C(=O)O)c2)c1=O] | (R)-3-((4-(3-aminopiperidin-1-yl)-3-(but-2-yn-1-yl)-2,6-dioxo-3,6-dihydropyrimidin-1(2H)-yl)methyl)benzoic acid |
| 25 | 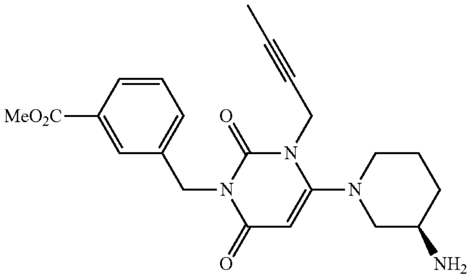 [SMILES: CC#CCn1c(N2CCC[C@@H](N)C2)cc(=O)n(Cc2cccc(C(=O)OC)c2)c1=O] | methyl (R)-3-((4-(3-aminopiperidin-1-yl)-3-(but-2-yn-1-yl)-2,6-dioxo-3,6-dihydropyrimidin-1(2H)-yl)methyl)benzoate |

TABLE 3-continued

| Exemplary DPP4 Inhibitors or their prodrugs | | |
|---|---|---|
| Cpd # | Chemical structure | Name |
| 26 | 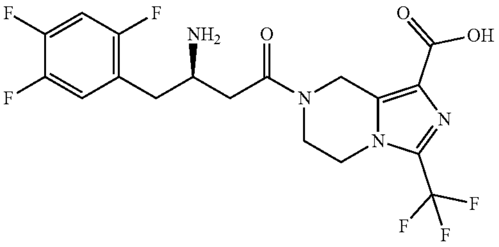 [SMILES: N[C@@H](CC(=O)N1CCn2c(C(F)(F)F)nc(C(=O)O)c2C1)Cc1cc(F)c(F)cc1F] | (R)-7-(3-amino-4-(2,4,5-trifluorophenyl)butanoyl)-3-(trifluoromethyl)-5,6,7,8-tetrahydroimidazo[1,5-a]pyrazine-1-carboxylic acid |
| 27 | 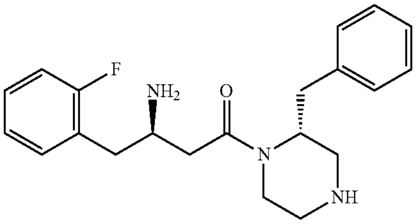 [SMILES: N[C@@H](CC(=O)N1CCNC[C@H]1Cc1ccccc1)Cc1ccccc1F] | (R)-3-amino-1-((R)-2-benzylpiperazin-1-yl)-4-(2-fluorophenyl)butan-1-one |
| 28 | 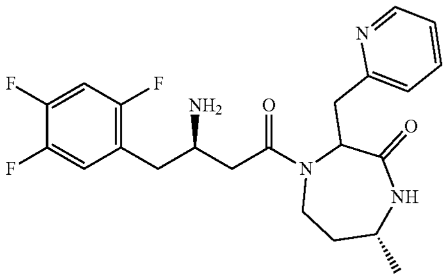 [SMILES: C[C@@H]1CCN(C(=O)C[C@H](N)Cc2cc(F)c(F)cc2F)C(Cc2ccccn2)C(=O)N1] | (7R)-4-((R)-3-amino-4-(2,4,5-trifluorophenyl)butanoyl)-7-methyl-3-(pyridin-2-ylmethyl)-1,4-diazepan-2-one |
| 29 | 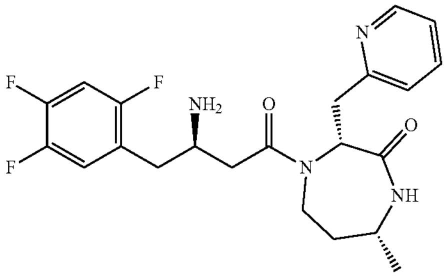 | (3R,7R)-4-((R)-3-amino-4-(2,4,5-trifluorophenyl)butanoyl)-7-methyl-3-(pyridin-2-ylmethyl)-1,4-diazepan-2-one |
| 30 | 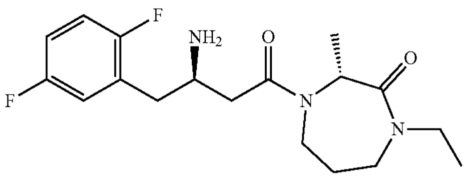 [SMILES: CCN1CCCN(C(=O)C[C@H](N)Cc2cc(F)ccc2F)[C@H](C)C1=O] | (R)-4-((R)-3-amino-4-(2,5-difluorophenyl)butanoyl)-1-ethyl-3-methyl-1,4-diazepan-2-one |
| 31 | 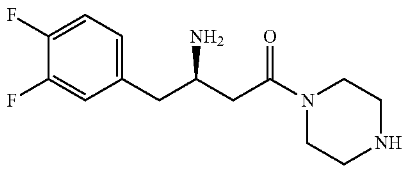 [SMILES: N[C@@H](CC(=O)N1CCNCC1)Cc1ccc(F)c(F)c1] | (R)-3-amino-4-(3,4-difluorophenyl)-1-(piperazin-1-yl)butan-1-one |

In an exemplary embodiment, the present disclosure provides a method as disclosed herein, such as a method for treating a pulmonary disease or lung condition in a subject suffering therefrom, comprising administering to the subject a DPP4 inhibitor or a pharmaceutically acceptable salt thereof that is compound 15. In some embodiments, compound 15 is administered by inhalation.

Pharmaceutical Compositions

The disclosure also provides in various embodiments a pharmaceutical composition comprising a therapeutically effective amount of one or more compounds as described herein, or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Tables 1 to 3 or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound or a pharmaceutically acceptable salt, stereoisomer, and/or tautomer thereof that is administered is governed by such considerations, and is the minimum amount necessary to regenerate AEC2 cell proliferation, or to inhibit DPP4, or both. Such amount may be below the amount that is toxic to normal cells or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg. Typical dose ranges are about 0.1 to about 400 mg/kg of patient body weight per day, with the typical initial range being about 50 to about 200 mg/kg/day. Oral unit dosage forms, such as tablets and capsules, may contain from about 0.1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment, such dosage forms contain from about 5 mg to about 50 mg of a compound (or a pharmaceutically acceptable salt, stereoisomer, or tautomer thereof) of the present disclosure. In any of the foregoing embodiments the dosage form can be administered one, two, three, or four times per day.

The compositions of the present disclosure can be administered orally, topically, parenterally, by inhalation or spray such as for pulmonary administration, or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, bard or soft capsules, syrups or elixirs.

In another aspect, also encompassed are pharmaceutical compositions suitable for single unit dosages that comprise a compound of the disclosure or its pharmaceutically acceptable stereoisomer, salt, or tautomer and a pharmaceutically acceptable carrier.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of the compound.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the present disclosure may also be administered in the form of suppositories for rectal administration. These compositions can be prepared by mixing the compounds with a suitable non-irritating excipient which is solid at ordinary temperatures but liquid at the rectal temperature and will therefore melt in the rectum to release the compound. Such materials are cocoa butter and polyethylene glycols.

Compositions for parenteral administrations are administered in a sterile medium. Depending on the vehicle used and concentration the concentration of the compounds in the formulation, the parenteral formulation can either be a suspension or a solution containing dissolved compound. Adjuvants such as local anesthetics, preservatives and buffering agents can also be added to parenteral compositions.

Oral Delivery of Gliptins, Systemic Exposure

The present disclosure also provides, in various embodiments, a method of treating a subject suffering from a pulmonary disorder, comprising administering to the subject a compound (i.e., gliptin) as disclosed herein formulated for oral administration of the gliptin. In an illustrative embodiment, the compound is chosen from linagliptin and saxagliptin. In various embodiments, the compound is formulated with one or more excipients into any oral dosage form, including tablets, troches, lozenges, aqueous or oily suspensions, dispersible powders or granules, emulsion, hard or soft capsules, syrups or elixirs.

An advantage of the present disclosure resides in the established safety and efficacy of FDA-approved gliptin compounds, such as linagliptin and saxagliptin, for use in therapeutic treatment of diabetes. As the examples below illustrate, however, recommended doses of the approved gliptin compounds by oral administration for labeled uses do not provide effective exposure in the lung for treating pulmonary diseases as disclosed herein, such as acute lung injury (ALI) and acute respiratory distress syndrome (ARDS). Accordingly, in various embodiments, the oral dose of gliptin compound for use in the inventive method ranges from about 5 times to about 15 times the dose that would be effective in treating diabetes in a subject suffering therefrom. Exemplifying the antidiabetic oral dose is a dose of the gliptin compound approved by the U.S. FDA for antidiabetic indications. In various embodiments, the oral dose is about 2 times to about 12 times, about 3 times to about 10 times, about 5 times to about 10 times, about 5 times to about 7 times, or about 8 times to about 12 times an effective antidiabetic dose, e.g., an approved oral dose. Illustrative doses include about 2, about 3, about 4, about 5, about 6, about 7, about 8, about 9, and about 10 times the approved oral dose. Thus, in an exemplary embodiment, the daily oral dose of saxagliptin is about 500 mg, the approved oral dose being 2.5 to 5 mg (QD). In another exemplary embodiment, the daily oral dose of linagliptin is about 50 to about 100 mg, whereas the approved oral dose is 5 mg (QD).

Pulmonary Delivery of Gliptin Salts, Inhalable Formulations

In some embodiments, the present disclosure provides salts or prodrugs of the gliptin compounds disclosed herein for pulmonary delivery. The compounds generally have at least one, including two and three, ionizable groups, e.g., amines, that are suitable for salt formation. Not just any pharmaceutically acceptable salt is appropriate for pulmonary delivery, however, as the salt must be compatible with, and non-toxic toward, lung tissue. This is especially important in embodiments wherein gliptin salts are administered for local and not systemic exposure. Thus, in various embodiments, the present disclosure provides for acid addition salts of any of the compounds disclosed herein. Illustrative acids include hydrochloric acid, sulfuric acid, hydrobromic acid, methanesulfonic acid, tartaric acid, palmitic acid, acetic acid, phosphoric acid, 1-hydroxy-2-naphthoic acid, ethanesulfonic acid, and fumaric acid.

The salts are suitable for pulmonary delivery to a subject, such as for treatment of a pulmonary disease or lung condition as disclosed herein. For example, in embodiments, local lung conditions include a spectrum of clinical syndromes generally having in common acute respiratory failure, illustrated by acute lung injury (ALI) and acute respiratory distress syndrome (ARDS). In additional embodiments, the local lung condition is interstitial lung diseases (ILDs) or idiopathic pulmonary fibrosis (IPF).

In accordance with established principles, formation of salts of the compounds increases their water solubility for greater ease in formulation of compositions suitable for pulmonary delivery. Pulmonary drug delivery technology is well-known to the skilled artisan, including choice of propellants, excipients, and delivery devices. For instance, minimally invasive Jung delivery of salts of the compounds disclosed herein is achieved, in some embodiments, using any combination of propellants, surfactants, non-aqueous inhalers, dry powder inhalers, metered dose inhalers, and jet or ultrasonic nebulizers known in the art. In various embodiments, an inhalable composition for pulmonary delivery aerosols and nebulized formulations of the compound.

Effective deposition of the salt into the lungs generally requires droplets less than 5 μm in diameter, in accordance with various embodiments. Delivery of fluid to the lungs generally requires a droplet delivery device to impart a momentum that is high enough to permit ejection out of the device, whilst sufficiently low to prevent deposition on the tongue or in the back of the throat. Droplets below 5 μm in diameter are transported almost entirely by entrainment in the air that carries them and not by their own momentum.

For therapeutic treatment of local lung conditions, such as IPF, ILDs, ALI, and ARDS, doses of the gliptin salts disclosed herein are considerably higher than doses in oral delivery formulations of the corresponding base gliptins for their approved therapies, e.g., in treatment of Type II diabetes. In various embodiments, the gliptins as disclosed herein are administered via pulmonary delivery, such as for the treatment of the lung diseases disclosed herein: this has an advantage of decreasing the overall dose and improving the therapeutic window of the gliptins. In illustrative embodiments, mouse lung pharmacokinetic parameters of sitagliptin, saxagliptin, vildagliptin and linagliptin showed that only one-fifth doses are required for pulmonary delivery to achieve similar lung drug exposure (see FIG. 6). In additional embodiments, the overall daily dose is reduced further by increasing dosing frequency from once a day to twice or three times a day. Thus, in various embodiments, a dose of a gliptin salt for pulmonary delivery in the inventive method is about 0.1, 0.3, 0.5, 0.7, 0.9, 1.0, 1.5, 2, 2.5, 3, 3.5, 4, 4.5, or about 5 times the dose of the base gliptin given by oral administration for approved uses. In further embodiments, the dose is about 0.1 to about 5, 0.1 to about 4, about 0.3 to about 3, about 0.5 to about 2.5, or about 0.9 to about 2 times the dose of the base gliptin given by oral administration for approved uses. In an exemplary embodiment, the dose of the gliptin salt in the inhalable formulation is about 3 times the dose of the corresponding base gliptin in an approved oral dosage form.

Screen for Identifying Compounds that Selectively Promote AEC2 Proliferation

To identify small molecules capable of proliferating AEC2s, as disclosed herein, we first established a culture system with primary human small airway epithelial cells (SAECs) from a commercial source. SAECs stain positively (>90%) for a number of AEC2 markers including surfactant protein C (SFPTC), and they store neutral lipids (indicating the presence of surfactant-storing bodies), indicating that they are primarily AEC2s. Optimizing a high content imaging assay that measures the total number of Ki67 positive AEC2s per well in mitogen-free conditions yielded a highly reproducible screening assay (Z'>0.55) when insulin-like growth factor 1 (IGF1) was used as a biologically-relevant positive proliferation control (FIG. 1A).

Figure 1C:
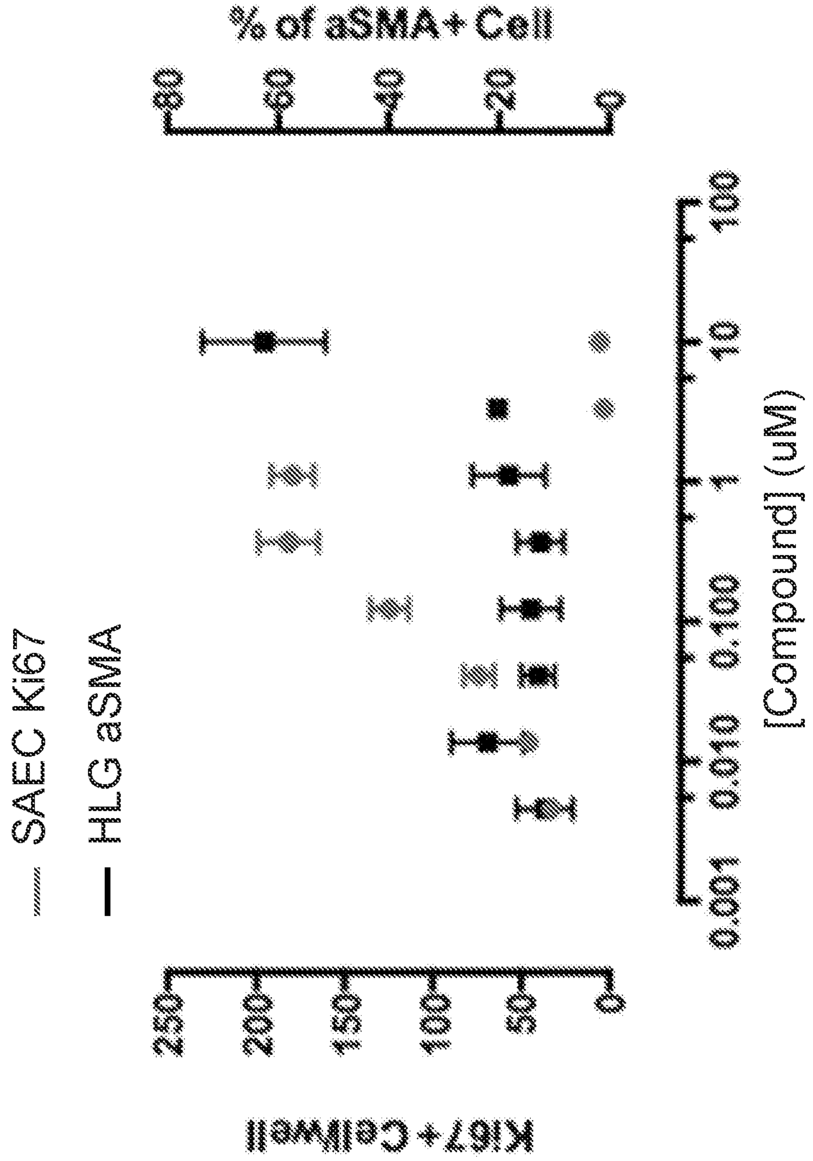

We then screened the comprehensive repurposing library ReFRAME for small molecules which increased S-phase AEC2s.[6] Transforming growth factor beta receptor (TGFBR) inhibitors were identified as a previously reported class of AEC2-proliferating molecules: this established confidence in the assay and cellular source. Among the top hits for which no biological mechanisms are reported were NVP-728 (an investigational DPP4 inhibitor; $EC_{50}$~500 nM: FIG. 1B) and siponimod (BAF312; an FDA-approved S1P1R modulator; $EC_{50}$~100 nM, FIG. 1C). When these molecules were tested against primary preparations of human pulmonary fibroblasts, they did not increase the total number, percent Ki67 positivity, or myofibroblast differentiation status of these cells at concentrations at which they promoted AEC2 proliferation (FIGS. 1B and 1C). These molecules therefore promote specific AEC2 proliferation without affecting myofibroblast activation or proliferation, which is undesirable in most disease contexts.

Figure 2A:
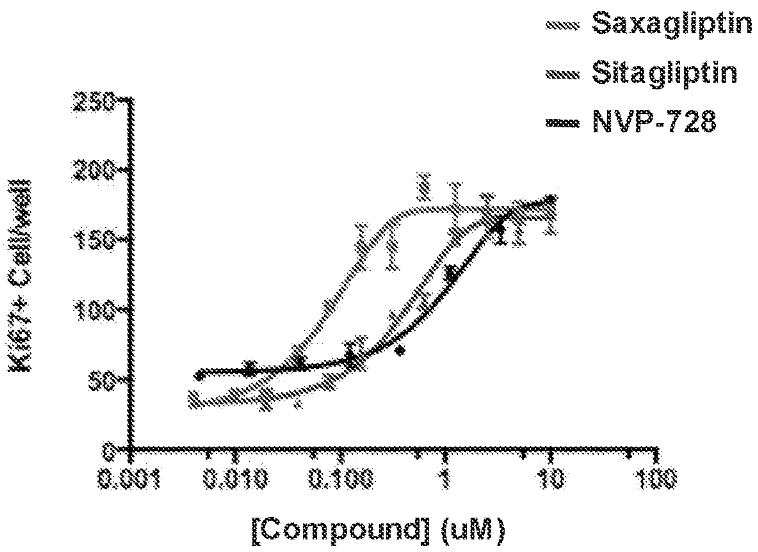
FIG. 2A-FIG. 2D.
Figure 2B:
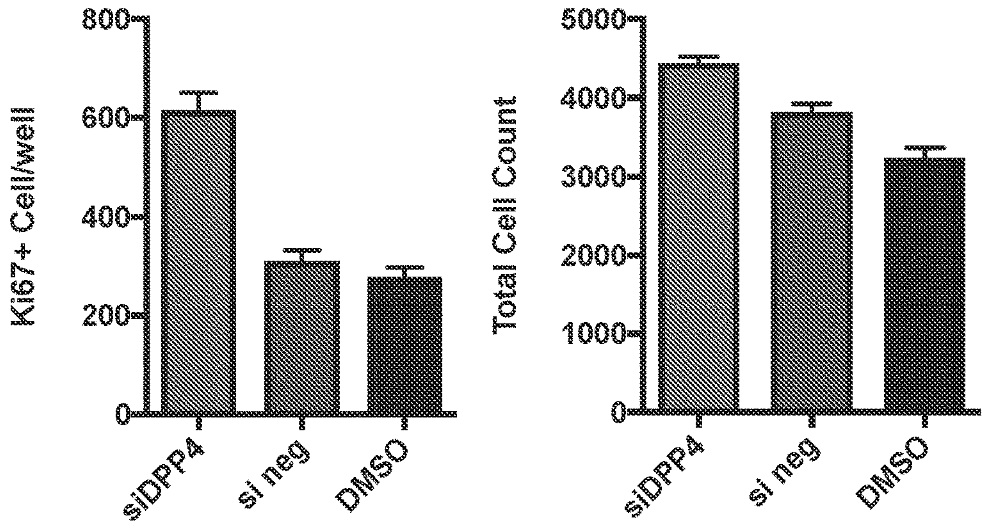

Confirming that NVP-728 and siponimod promote AEC2 proliferation through their reported mechanisms of action, we performed further experiments with additional pharmacological and genetic manipulations of these signaling pathways. We found that two additional FDA-approved DPP4 inhibitors, Saxagliptin and Sitagliptin, promote AEC2 proliferation to the same magnitude as NVP-728 (FIG. 2A) and that cellular $EC_{50}$ values tracked with $IC_{50}$ values reported for inhibition of recombinant enzyme (0.6 nM, Saxagliptin: 18 nM, Sitagliptin: 14 nM, NVP-728). Similarly, we found that siRNA-mediated knockdown of DPP4 levels promoted an increase in total and Ki67 positive AEC2 cell numbers (FIG. 2B).

Figure 2C:
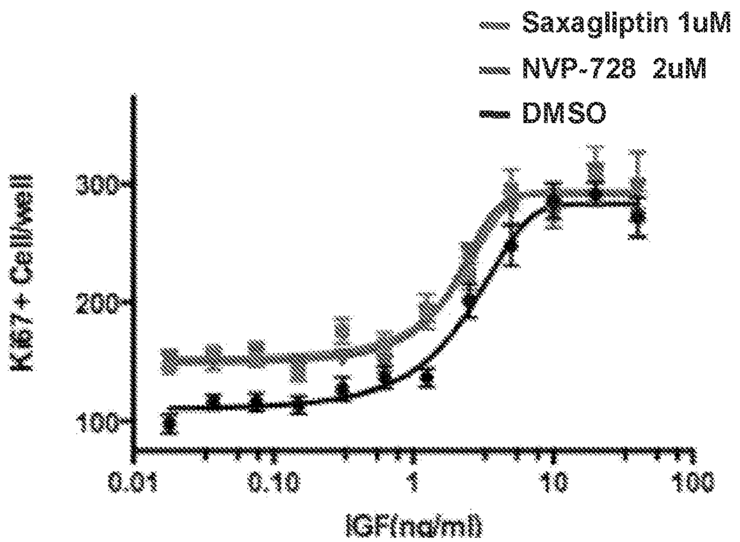
Figure 2D:
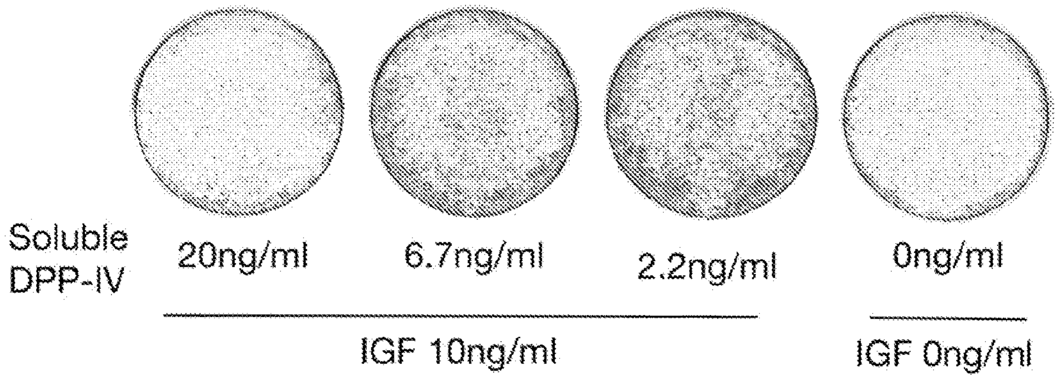
Figure 4:
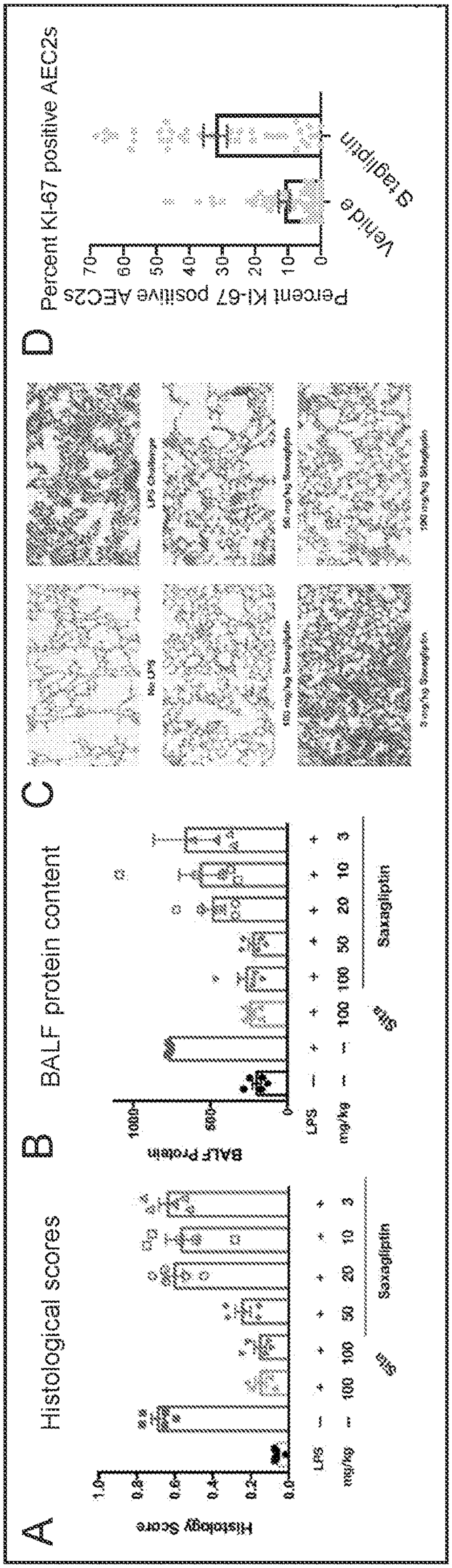
FIG. 4A-FIG. 4D. High doses of DPP4 inhibitors Saxagliptin and Sitagliptin promote repair in an acute lung injury model. Histological scores (FIG. 4A) and BALF protein level (FIG. 4B) from mice orally treated with the indicated concentrations of Saxagliptin and Sitagliptin and challenged with intratracheal LPS administration. Quantification of percent positive AEC2s, cells that stain copositive for SFPTC and KI-67 at day 3 of the study (FIGS. 4C and 4D).
Figure 5:
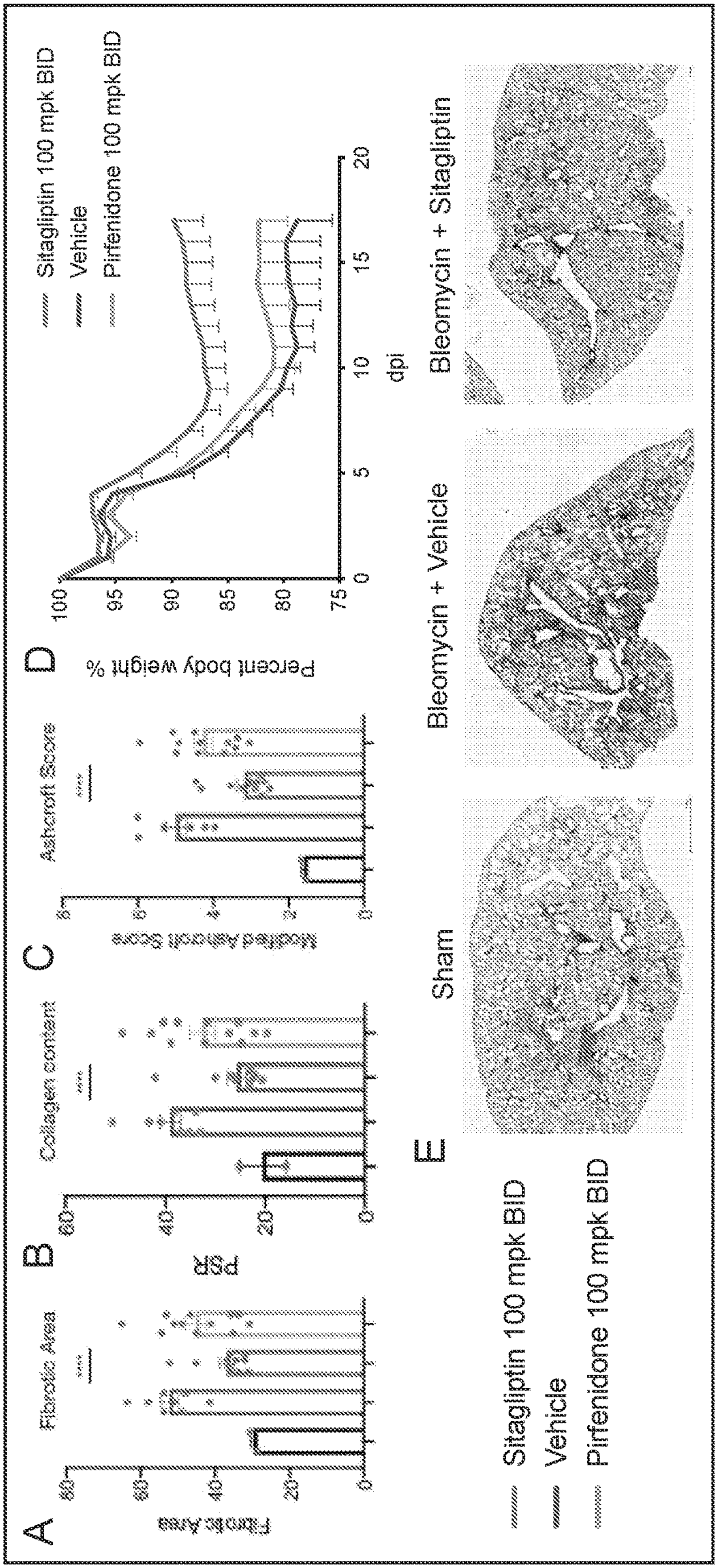
FIG. 5A-FIG. 5E. Oral Sitagliptin displays ameliorative efficacy in bleomycin-induced lung fibrosis. Fibrotic area measurements (FIG. 5A), Picrosirius Red measurements (FIG. 5B), modified Ashcroft scores (FIG. 5C), percent body weight (FIG. 5D), and representative Masson's Trichome stained histological sections (FIG. 5E) from mice treated with Sitagliptin or Pirfenidone (both 100 mg/kg BID) and challenged with intratracheal bleomycin administration.

DPP4, a dipeptidyl protease, degrades proteinaceous signaling molecules to control the duration and magnitude of the signaling responses of its substrates. Among the most highly expressed DPP4 substrates in AEC2s is IGF1, which has been previously reported as an autocrine growth factor for this cell type. We found that treatment of AEC2s with DPP4 inhibitors sensitized cells to the proliferative effects of IGF1 (FIG. 2C), likely through inhibiting degradation of the signaling molecule. In this context, we found that when AEC2s were stimulated with exogenous IGF1 that this proliferative effect is inhibited by increasing amounts of recombinant DPP4 (FIG. 2D). These results together demonstrate that DPP4 inhibition is an operative mechanism for promoting AEC2 cell expansion.

Confirming that siponimod promotes AEC2 expansion through an S1PR1-targeted mechanism, we evaluated a panel of S1PR modulators with varying affinities for different receptor subtypes (FIG. 3). Pan-S1PR modulators (e.g., FTY-720), S1PR1/S1PR5 selective (e.g., Ozanimod), and S1PR1 selective (e.g., SEW-2871) modulators were active in AEC2 proliferation assays (FIG. 3). In contrast to S1PR1, S1PR5 is not expressed in AEC2s (not shown), indicating that modulating S1PR1 activity is the common pharmacologically relevant target for promoting AEC2 growth in this context. The literature also confirms a role for S1PR1 agonism in protecting AEC2s and lung function in the adult organism. Studies from Stone et al.[9] and Diab et al.[10] have shown that when the adult mouse was challenged in the context of an ischemia reperfusion model or an emphysema model that S1PR1 ligands FTY720 and SEW2871 inhibited apoptosis and inflammatory cytokine release in alveolar epithelium, indicating that S1P receptor agonism can be an AEC2-relevant mechanism for intervening in various disease states.

In an exemplary embodiment, the two widely used medications Sitagliptin and Saxagliptin, in a lipolysaccharide (LPS) lung injury model, demonstrated that proliferative activity of the medications translates into protective efficacy in small rodent models of lung damage and fibrosis. This model is frequently used to simulate damage to the lower airway as LPS induces loss of alveolar integrity and AEC1/2 cell death. Oral administration of both Sitagliptin and Saxagliptin treatment resulted in dramatic improvements in all measured metrics including histological scoring and BALF protein and cellular content (a measure of permeability and inflammation). Importantly, to achieve efficacy in these models, doses were required (minimal efficacious dose=50 mg/kg for Saxagliptin; 100 mg/kg Sitagliptin) that are significantly greater than those used for rodent models of diabetes: efficacy in the oral glucose tolerance test (OGTT) model is observed with 3-30 mg/kg for Sitagliptin and 0.5-5 mg/kg for Saxagliptin.

It was further determined the degree to which gliptin-induced AEC2 expansion is responsible for drug efficacy in the LPS model. Time course studies established that high doses of Sitagliptin do not affect cytokine or bronchoalveolar lavage fluid (BALF) levels at early timepoints. Only at later time points does Sitagliptin promote changes in cytokine and BALF protein levels. Further, Sitagliptin promotes a substantial increase in proliferative AEC2s (KI-67 SFPTC double positive cells), but it does not significantly increase the total number of cells (all nuclei) or Ki-67 positive cells (largely immune cells) in the lung. Together these data demonstrate that DPP4 inhibition promotes lung repair through proliferative regeneration (FIGS. 4A-4D).

In another illustrative embodiment, Sitagliptin was evaluated for its effects on bleomycin-induced fibrosis in mouse. In this context, intratracheal bleomycin administration to the mouse induces death to the AEC2 population, a feature which likely mimics the loss of AEC2s observed in human disease.[4] High doses of Sitagliptin (100 mg/kg qD or BID) resulted in robust protection in multiple metrics of disease progression including weight loss, survival, BALF protein content, hydroxyproline content, and percent fibrotic area histological scoring (FIGS. 5A-5E). Importantly, we found that these effects were comparable to or greater than the approved drug pirfenidone. In addition to Pirfenidone, co-treatment of Sitagliptin with the approved drug Nintedanib (Ofev) resulted in synergistic protection in the bleomycin model (pharmacological synergism determined by Bliss independence calculations). This combinatorial effect on disease progression suggests that inducing repair through proliferation is a complementary mechanism for treating disease because Nintedanib is only expected to inhibit myofibroblast activity. This combinatorial treatment strategy results in increased patient benefit, as this approach would both promote repair of the alveolus as well as decrease further disease progression. High doses are needed for target coverage in the lung (substantiated by PK described below) for in vivo efficacy.

In a further illustrative embodiment, as detailed in the examples herein, dutogliptin boronate (15) as a prodrug of dutogliptin provided prolonged lung retention through inhalation. Dutogliptin (1) is a boronic acid based DPP4 inhibitor that was studied in Phase 2/3 clinical trials. Once-a-day oral doses of 200 mg and 400 mg statistically reduced HbA1c versus placebo. In a separate mouse IT pharmacokinetic study, the boronate (15) was shown to convert to the active drug dutogliptin in both plasma and lung The active drug exposure in the lung was much higher than that from dutogliptin dosed itself and much longer lasting (see Table 8A/B). In a Bleomycin induced lung fibrosis model, the boronate (15) reduced BALF protein level compared to vehicle when dosed IT once every four days (see FIG. 8).

Numbered references in the preceding sections are as follows:

[1] Hogan, B. L., Barkauskas, C. E., Chapman, H. A., Epstein, J. A., Jain, R., Hsia, C. C., Niklason, L., Calle, E., Le, A., Randell, S. H., Rock, J., Snitow, M., Krummel, M., Stripp, B. R., Vu, T., White, E. S., Whitsett, J. A., and Morrisey, E. E. (2014) Repair and regeneration of the respiratory system: complexity, plasticity, and mechanisms of lung stem cell function. *Cell Stem Cell* 15. 123-138

[2] Barkauskas, C. E., Cronce, M. J., Rackley, C. R., Bowie, E. J., Keene, D. R., Stripp, B. R., Randell, S. H., Noble, P. W., and Hogan, B. L. (2013) Type 2 alveolar cells are stem cells in adult lung, *J Clin Invest* 123, 3025-3036.

[3] Noble, P. W., Barkauskas, C. E., and Jiang, D. (2012) Pulmonary fibrosis: patterns and perpetrators, *J Clin Invest* 122, 2756-2762.

[4] Liang, J., Zhang, Y., Xie, T., Liu, N., Chen, H., Geng, Y., Kurkciyan, A., Mena, J. M., Stripp, B. R., Jiang, D., and Noble, P. W. (2016) Hyaluronan and TLR4 promote surfactant-protein-C-positive alveolar progenitor cell renewal and prevent severe pulmonary fibrosis in mice, *Nat Med* 22, 1285-1293.

[5] Thompson, B. T., Chambers, R. C., and Liu, K. D. (2017) Acute Respiratory Distress Syndrome, *N Engl J Med* 377, 1904-1905.

[6] Janes, J., Young, M. E., Chen, E., Rogers, N. H., Burgstaller-Muehlbacher, S., Hughes, L. D., Love, M. S., Hull, M. V., Kuhen, K. L., Woods, A. K., Joseph, S. B., Petrassi, H. M., McNamara, C. W., Tremblay, M. S., Su, A. I., Schultz, P. G., and Chatterjee, A. K. (2018) The ReFRAME library as a comprehensive drug repurposing library and its application to the treatment of cryptosporidiosis, *Proc Natl Acad Sci USA* 115, 10750-10755.

[7] Xu, J., Wang, J., He, M., Han, H., Xie, W., Wang, H., and Kong, H. (2018) Dipeptidyl peptidase IV (DPP-4) inhibition alleviates pulmonary arterial remodeling in experimental pulmonary hypertension, *Lab Invest* 98, 1333-1346.

[8] Kawasaki, T., Chen, W., Htwe, Y. M., Tatsumi, K., and Dudek, S. M. (2018) DPP4 inhibition by sitagliptin attenuates LPS-induced lung injury in mice, *Am J Physiol Lung Cell Mol Physiol.*

[9] Stone, M. L., Sharma, A. K., Zhao, Y., Charles, E. J., Huerter, M. E., Johnston, W. F., Kron, I. L., Lynch, K. R., and Laubach, V. E. (2015) Sphingosine-1-phosphate receptor 1 agonism attenuates lung ischemia-reperfusion injury. *Am J Physiol Lung Cell Mol Physiol* 308, L1245-1252.

[10] Diab, K. J., Adamowicz, J. J., Kamocki, K., Rush, N. I., Garrison, J., Gu, Y., Schweitzer, K. S., Skobeleva, A., Rajashekhar, G., Hubbard, W. C., Berdyshev. E. V., and Petrache, I. (2010) Stimulation of sphingosine 1-phosphate signaling as an alveolar cell survival strategy in emphysema, *Am J Respir Crit Care Med* 181, 344-352.

Additional embodiments of the present disclosure are set forth in the following non-limiting examples.

EXAMPLES

Example 1: DPP4 Activity and AEC2 Cell Proliferation Assays

DPP4 activity assay. Human DPP4 activity assay data were obtained using a DPP4 Activity Assay Kit (Sigma- Aldrich, MAK088) according to the manufacturer's instructions. Briefly, 10 μL of DPP4 Assay Buffer was transferred per well in low volume 384-well plates before transferring 10 μL of diluted compound dissolved in DPP4 assay buffer. 5 μL of Master Reaction Mix containing a fluorescent substrate that becomes fluorescent upon cleavage by the enzyme. Fluorescence intensity measurements were recorded at 1-minute time intervals over the course of 20 minutes using an Envision Multimode Plate Reader (PerkinElmer).

AEC2 proliferation assay. Primary human AEC2s were plated at a density of 1,500 cells per well in black 384-well plates (Greiner) coated with 10 ug/mL. Laminin (Life Technologies) in 50 μL of Small Airway Epithelial Cell Growth Medium (Lonza) without EGF, retinoic acid and with 5% BPE. 100 nL of compound dissolved in DMSO was then delivered using a Biomek FX instrument (Beckman Coulter) fitted with a pintool head (V&P Scientific). After 96 hours of growth at 37° C., cells were fixed with 4% paraformaldehyde, washed three times with PBS, and then immunostained for KI-67 positivity (1:1000, Abcam, ab15580) overnight at 4° C. After three additional washes, incubation with secondary AlexaFluor conjugated secondary antibody for 1 hour at room temperature and exposure to 10 μg/mL Hoechst 33342 (Life Technologies), plates were scaled, and then quantitative high content imaging carried out on CellInsight CX5 HCS instrument (ThermoFisher).

Compounds subjected to the assays and corresponding results are presented in Table 4 below.

TABLE 4

Inhibition of DPP4 ($IC_{50}$), Promotion of AEC2 Proliferation ($EC_{50}$) (NT = not tested)

| Cpd # | Chemical structure | Name | DPPIV $IC_{50}$ (nM) | AEC2 $EC_{50}$ (μM) |
|---|---|---|---|---|
| 1 | 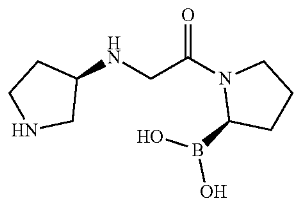 [SMILES: O=C(CN[C@@H]1CCNC1)N1CCC[C@H]1B(O)O] | ((R)-1-(((R)-pyrrolidin-3-yl)glycyl)pyrrolidin-2-yl)boronic acid (Dutogliptin) | 122 | 0.28 |
| 2 | 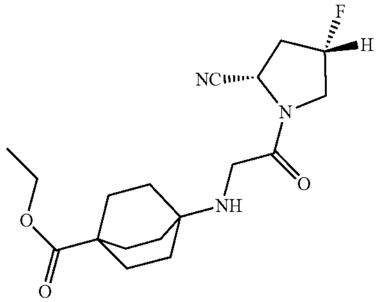 [SMILES: CCOC(=O)C12CCC(NCC(=O)N3C[C@@H](F)C[C@H]3C#N)(CC1)CC2] | ethyl 4-((2-((2S,4S)-2-cyano-4-fluoropyrrolidin-1-yl)-2-oxoethyl)amino)bicyclo[2.2.2]octane-1-carboxylate (Bisegliptin) | 2.2 | NT |
| 3 | 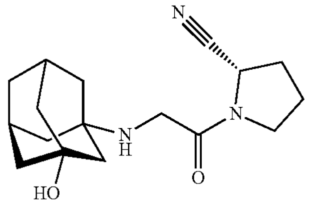 | (2S)-1-(((1S,3R,5S)-3-hydroxyadamantan-1-yl)glycyl)pyrrolidine-2-carbonitrile (vildagliptin) | 4.8 | 0.16 |
| 4 | 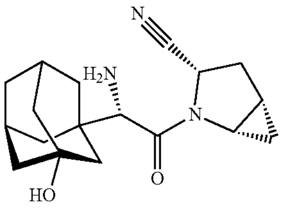 | (1S,3S,5S)-2-((2S)-2-amino-2-((1S,3R,5S)-3-hydroxyadamantan-1-yl)acetyl)-2-azabicyclo[3.1.0]hexane-3-carbonitrile (saxaglitptin) | 6 | 0.65 |

TABLE 4-continued

| Cpd # | Chemical structure | Name | DPPIV $IC_{50}$ (nM) | AEC2 $EC_{50}$ (μM) |
|---|---|---|---|---|
| | Inhibition of DPP4 ($IC_{50}$), Promotion of AEC2 Proliferation ($EC_{50}$) (NT = not tested) | | | |
| 5 | 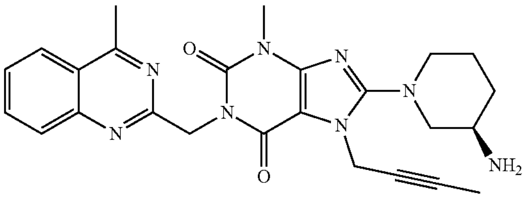 [SMILES: CC#CCn1c(N2CCC[C@@H](N)C2)nc2c1c(=O)n(Cc1nc(C)c3ccccc3n1)c(=O)n2C] | (R)-8-(3-aminopiperidin-1-yl)-7-(but-2-yn-1-yl)-3-methyl-1-((4-methylquinazolin-2-yl)methyl)-3,7-dihydro-1H-purine-2,6-dione (linagliptin) | 0.2 | 0.26 |
| 6 | 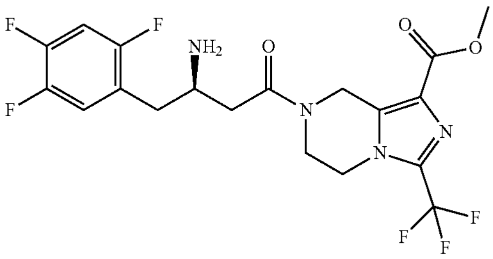 [SMILES: COC(=O)c1nc(C(F)(F)F)n2c1CN(C(=O)C[C@H](N)Cc1cc(F)c(F)cc1F)CC2] | methyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (Retagliptin) | 0.6 | NT |
| 7 | 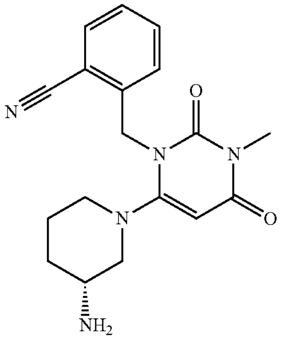 [SMILES: Cn1c(=O)cc(N2CCC[C@@H](N)C2)n(Cc2ccccc2C#N)c1=O] | (R)-2-((6-(3-aminopiperidin-1-yl)-3-methyl-2,4-dioxo-3,4-dihydropyrimidin-1(2H)-yl)methyl)benzonitrile (alogliptin) | 0.9 | 0.11 |
| 8 | 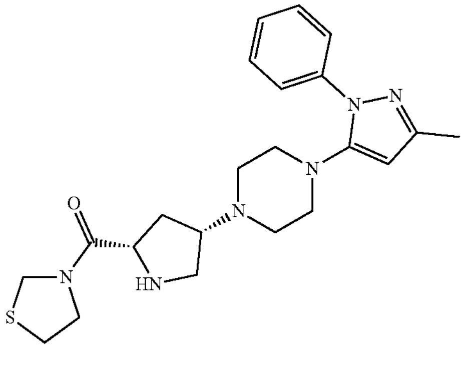 [SMILES: Cc1cc(N2CCN([C@@H]3CN[C@H](C(=O)N4CCSC4)C3)CC2)n(-c2ccccc2)n1] | ((2S,4S)-4-(4-(3-methyl-1-phenyl-1H-pyrazol-5-yl)piperazin-1-yl)pyrrolidin-2-yl)(thiazolidin-3-yl)methanone (Teneligliptin) | 0.8 | NT |
| 9 | 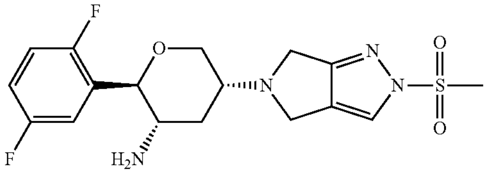 [SMILES: CS(=O)(=O)n1cc2c(n1)CN([C@H]1CO[C@H](c3cc(F)ccc3F)[C@@H](N)C1)C2] | (2R,3S,5R)-2-(2,5-difluorophenyl)-5-(2-(methylsulfonyl)-2,6-dihydropyrrolo[3,4-c]pyrazol-5(4H)-yl)tetrahydro-2H-pyran-3-amine (omarigliptin) | 0.8 | 0.043 |

TABLE 4-continued

| Cpd # | Chemical structure | Name | DPPIV $IC_{50}$ (nM) | AEC2 $EC_{50}$ (μM) |
|---|---|---|---|---|
| | Inhibition of DPP4 ($IC_{50}$), Promotion of AEC2 Proliferation ($EC_{50}$) (NT = not tested) | | | |
| 10 | 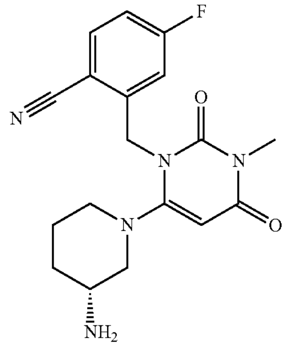 [SMILES: Cn1c(=O)cc(N2CCC[C@@H](N)C2)n(Cc2cc(F)ccc2C#N)c1=O] | (R)-2-((6-(3-aminopiperidin-1-yl)-3-methyl-2,4-dioxo-3,4-dihydropyrimidin-1(2H)-yl)methyl)-4-fluorobenzonitrile (Trelagliptin) | 0.7 | 0.067 |
| 11 | 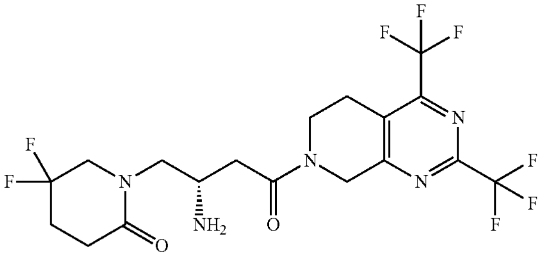 [SMILES: N[C@@H](CC(=O)N1CCc2c(nc(C(F)(F)F)nc2C(F)(F)F)C1)CN1CC(F)(F)CCC1=O] | (S)-1-(2-amino-4-(2,4-bis(trifluoromethyl)-5,8-dihydropyrido[3,4-d]pyrimidin-7(6H)-yl)-4-oxobutyl)-5,5-difluoropiperidin-2-one (Gemigliptin) | 4.1 | 0.22 |
| 12 | 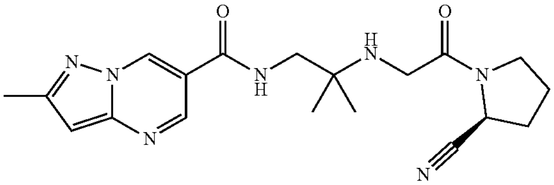 [SMILES: Cc1cc2ncc(C(=O)NCC(C)(C)NCC(=O)N3CCC[C@H]3C#N)cn2n1] | (S)-N-(2-((2-(2-cyanopyrrolidin-1-yl)-2-oxoethyl)amino)-2-methylpropyl)-2-methylpyrazolo[1,5-a]pyrimidine-6-carboxamide (Anagliptin) | 11.4 | 0.11 |
| 13 | 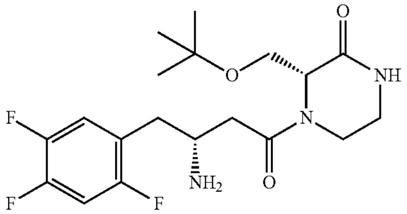 [SMILES: CC(C)(C)OC[C@@H]1C(=O)NCCN1C(=O)C[C@H](N)Cc1cc(F)c(F)cc1F] | (R)-4-((R)-3-amino-4-(2,4,5-trifluorophenyl)butanoyl)-3-(tert-butoxymethyl)piperazin-2-one (evogliptin) | 0.3 | 0.015 |
| 14 | 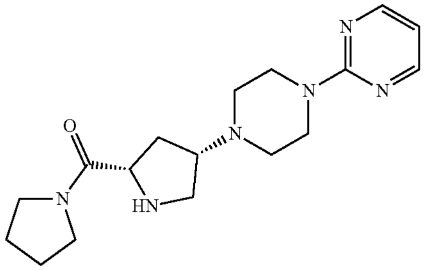 [SMILES: O=C([C@@H]1C[C@H](N2CCN(c3ncccn3)CC2)CN1)N1CCCC1] | ((2S,4S)-4-(4-(pyrimidin-2-yl)piperazin-1-yl)pyrrolidin-2-yl)(pyrrolidin-1-yl)methanone (gosogliptin) | 3.3 | 0.11 |

TABLE 4-continued

Inhibition of DPP4 ($IC_{50}$), Promotion of AEC2 Proliferation ($EC_{50}$) (NT = not tested)

| Cpd # | Chemical structure | Name | DPPIV $IC_{50}$ (nM) | AEC2 $EC_{50}$ (μM) |
|---|---|---|---|---|
| 15 | 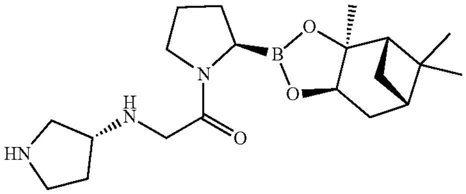 [SMILES: CC1(C)[C@@H]2C[C@H]3OB([C@@H]4CCCN4C(=O)CN[C@@H]4CCNC4)O[C@@]3(C)[C@H]1C2] | 2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl)ethan-1-one | NT | NT |
| 16 | 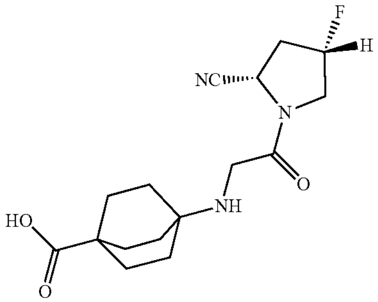 [SMILES: N#C[C@@H]1C[C@H](F)CN1C(=O)CNC12CCC(C(=O)O)(CC1)CC2] | 4-((2-((2S,4S)-2-cyano-4-fluoropyrrolidin-1-yl)-2-oxoethyl)amino)bicyclo[2.2.2]octane-1-carboxylic acid | 1.2 | NT |
| 17 | 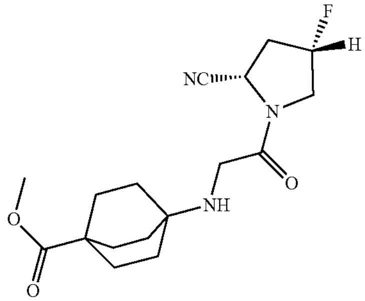 [SMILES: COC(=O)C12CCC(NCC(=O)N3C[C@@H](F)C[C@H]3C#N)(CC1)CC2] | methyl 4-((2-((2S,4S)-2-cyano-4-fluoropyrrolidin-1-yl)-2-oxoethyl)amino)bicyclo[2.2.2]octane-1-carboxylate | 1.0 | NT |
| 18 | 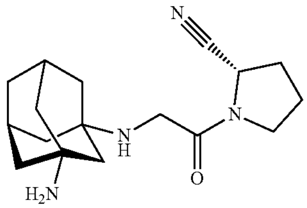 | (2S)-1-(((1S,3R,5R)-3-aminoadamantan-1-yl)glycyl)pyrrolidine-2-carbonitrile | 38 | NT |
| 19 | 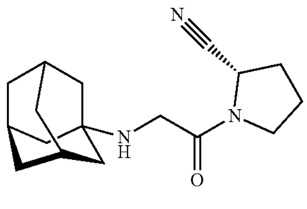 | (2S)-1-(((1r,3R,5S)-adamantan-1-yl)glycyl)pyrrolidine-2-carbonitrile | 15 | NT |
| 20 | 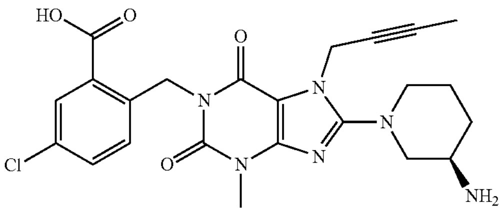 [SMILES: CC#CCn1c(N2CCC[C@@H](N)C2)nc2c1c(=O)n(Cc1ccc(Cl)cc1C(=O)O)c(=O)n2C] | (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoic acid | 3.7 | NT |

TABLE 4-continued

| Cpd # | Chemical structure | Name | DPPIV $IC_{50}$ (nM) | AEC2 $EC_{50}$ (μM) |
|---|---|---|---|---|
| | Inhibition of DPP4 ($IC_{50}$), Promotion of AEC2 Proliferation ($EC_{50}$) (NT = not tested) | | | |
| 21 | 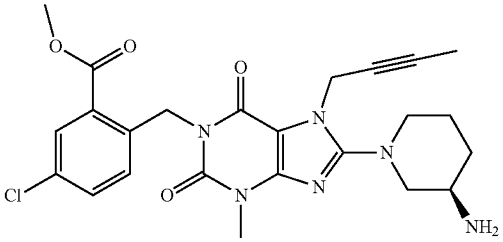 [SMILES: CC#CCn1c(N2CCC[C@@H](N)C2)nc2c1c(=O)n(Cc1ccc(Cl)cc1C(=O)OC)c(=O)n2C] | methyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate | 31 | NT |
| 22 | 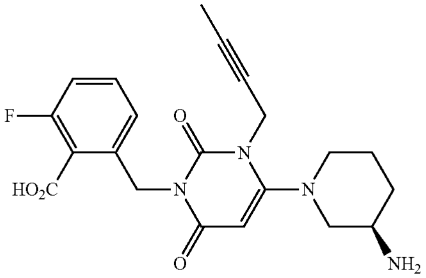 [SMILES: CC#CCn1c(N2CCC[C@@H](N)C2)cc(=O)n(Cc2cccc(F)c2C(=O)O)c1=O] | (R)-2-((4-(3-aminopiperidin-1-yl)-3-(but-2-yn-1-yl)-2,6-dioxo-3,6-dihydropyrimidin-1(2H)-yl)methyl)-6-fluorobenzoic acid | 3 | NT |
| 23 | 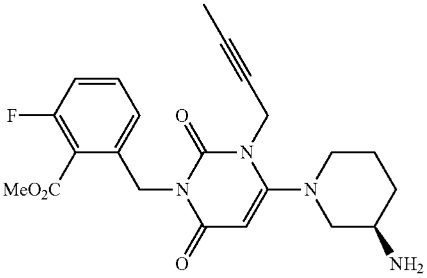 | methyl (R)-2-((4-(3-aminopiperidin-1-yl)-3-(but-2-yn-1-yl)-2,6-dioxo-3,6-dihydropyrimidin-1(2H)-yl)methyl)-6-fluorobenzoate | 74 | NT |
| 24 | 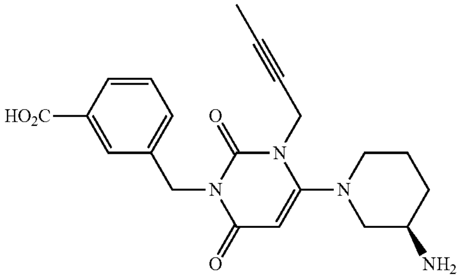 [SMILES: CC#CCn1c(N2CCC[C@@H](N)C2)cc(=O)n(Cc2cccc(C(=O)O)c2)c1=O] | (R)-3-((4-(3-aminopiperidin-1-yl)-3-(but-2-yn-1-yl)-2,6-dioxo-3,6-dihydropyrimidin-1(2H)-yl)methyl)benzoic acid | 3 | NT |
| 25 | 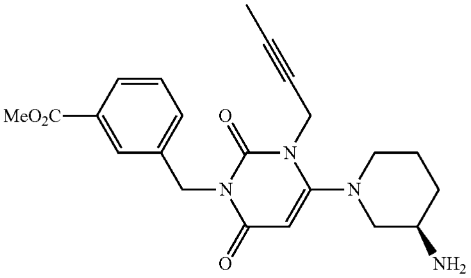 [SMILES: CC#CCn1c(N2CCC[C@@H](N)C2)cc(=O)n(Cc2cccc(C(=O)OC)c2)c1=O] | methyl (R)-3-((4-(3-aminopiperidin-1-yl)-3-(but-2-yn-1-yl)-2,6-dioxo-3,6-dihydropyrimidin-1(2H)-yl)methyl)benzoate | 6 | NT |

TABLE 4-continued

Inhibition of DPP4 ($IC_{50}$), Promotion of AEC2 Proliferation ($EC_{50}$) (NT = not tested)

| Cpd # | Chemical structure | Name | DPPIV $IC_{50}$ (nM) | AEC2 $EC_{50}$ (μM) |
|---|---|---|---|---|
| 26 | 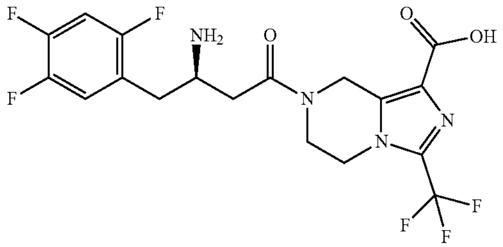 [SMILES: N[C@@H](CC(=O)N1CCn2c(C(F)(F)F)nc(C(=O)O)c2C1)Cc1cc(F)c(F)cc1F] | (R)-7-(3-amino-4-(2,4,5-trifluorophenyl)butanoyl)-3-(trifluoromethyl)-5,6,7,8-tetrahydroimidazo[1,5-a]pyrazine-1-carboxylic acid | 0.8 | NT |
| 27 | 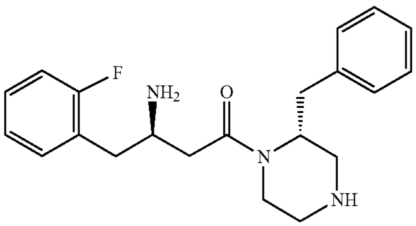 [SMILES: N[C@@H](CC(=O)N1CCNC[C@H]1Cc1ccccc1)Cc1ccccc1F] | (R)-3-amino-1-((R)-2-benzylpiperazin-1-yl)-4-(2-fluorophenyl)butan-1-one | NT | NT |
| 28 | 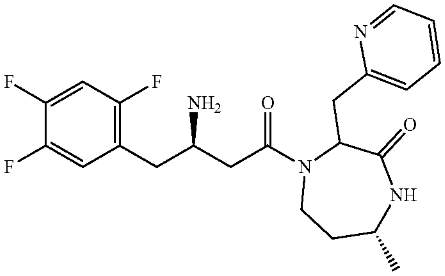 [SMILES: C[C@@H]1CCN(C(=O)C[C@H](N)Cc2cc(F)c(F)cc2F)C(Cc2ccccn2)C(=O)N1] | (7R)-4-((R)-3-amino-4-(2,4,5-trifluorophenyl)butanoyl)-7-methyl-3-(pyridin-2-ylmethyl)-1,4-diazepan-2-one | NT | NT |
| 29 | 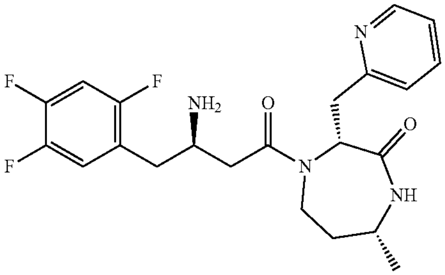 [SMILES: C[C@@H]1CCN(C(=O)C[C@H](N)Cc2cc(F)c(F)cc2F)[C@H](Cc2ccccn2)C(=O)N1] | (3R,7R)-4-((R)-3-amino-4-(2,4,5-trifluorophenyl)butanoyl)-7-methyl-3-(pyridin-2-ylmethyl)-1,4-diazepan-2-one | NT | NT |
| 30 | 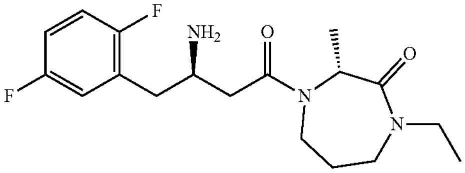 [SMILES: CCN1CCCN(C(=O)C[C@H](N)Cc2cc(F)ccc2F)[C@H](C)C1=O] | (R)-4-((R)-3-amino-4-(2,5-difluorophenyl)butanoyl)-1-ethyl-3-methyl-1,4-diazepan-2-one | NT | NT |
| 31 | 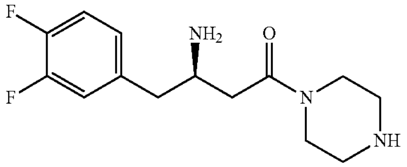 [SMILES: N[C@@H](CC(=O)N1CCNCC1)Cc1ccc(F)c(F)c1] | (R)-3-amino-4-(3,4-difluorophenyl)-1-(piperazin-1-yl)butan-1-one | NT | NT |

Example 2: In Vitro Characterization of Approved and Investigational DPP4 Inhibitors Identified from a high content imaging screen of ReFRAME, an inhibitor of dipeptidyl peptidase 4 (DPP4), from a drug class termed 'gliptins', was found to efficaciously expand alveolar type 2 cells in vitro. To better characterize this phenomenon across this compound class, we obtained commercially available and resynthesized versions of approved and late-stage investigational gliptins as shown in Table 5. All material was found to inhibit DPP4 enzymatic activity with similar potencies to those reported in the literature, suggesting high confidence in used material used. All gliptins evaluated except for Teneligliptin were found to induce a proliferative phenotype in AEC2s with potencies from 0.1-4 μM in cell culture. Gliptins do not proliferate pulmonary fibroblasts. A mechanism involving the inhibited degradation of autocrine growth factors was demonstrated to be responsible for the observed proliferative phenotype.

TABLE 5

DPP4 inhibitory activity and AEC2 proliferative activity of approved and investigational DPP4 inhibitors (NT = not tested).

| Drug | Approved | Marketed by | Reported DPP4 $IC_{50}$ (nM) | Observed DPP4 $IC_{50}$ (nM) | AEC2 proliferation (μM) |
|---|---|---|---|---|---|
| Sitagliptin | 2006 (US) | Merck | 18 | 4.5 | 0.56 |
| Vildagliptin | 2007 (EU) | Novartis | 2.3 | 4.8 | 0.16 |
| Saxagliptin | 2009 (US) | BMS-AZ | 3 | 6 | 0.65 |
| Linagliptin | 2011 (US) | Lilly - BI | 1 | 0.2 | 0.26 |
| Gemigliptin | 2012 (Korea) | LG life sciences | 7 | 4.1 | 0.22 |
| Anagliptin | 2012 (Japan) | Sanwa - Kowa | 3.8 | 11.4 | 0.11 |
| Teneligliptin | 2012 (Japan) | Mitsubishi- Daiichi | 1 | 0.8 | NT |
| Alogliptin | 2013 (US) | Takeda | 10 | 0.9 | 0.11 |
| Trelagliptin | 2015 (Japan) | Takeda | 4 | 0.7 | 0.067 |
| Omarigliptin | 2015 (Japan) | Merck | 1.6 | 0.8 | 0.043 |
| Evogliptin | 2015 (Korea) | Dong-A ST | 0.7 | 0.3 | 0.015 |
| Gosogliptin | 2016 (Russia) | Pfizer | 12.9 | 3.3 | 0.11 |
| Dutogliptin | Phase 3 | Phenomix | 25 | 122 | 0.28 |

Example 3: In Vivo Efficacy Activity of Gliptins in Mouse Models of Lung Injury and Fibrosis Experimental Methods of Acute Lung Injury (ALI) Model LPS from *E. coli* I111:B4 (Sigma) was used to induce acute lung injury in mice. Body weight matched (19 gram~22 gram) female C57BL/6J mice at 9-11 weeks of age were selected to use in ALI model.

For orally delivered DPP4 inhibitors, compounds were dissolved in PBS resulting in clear solution. Vehicle control or DPP4 inhibitors were dosed at 10 ml/kg through oral gavage once or twice a day selected based on PK profile. For intratracheally delivered DPP4 inhibitors, compounds were dissolved in PBS resulting in clear solution. Vehicle control or DPP4 inhibitors were dosed at 2 ml/kg through a 22 g flexible catheter every other day.

LPS (1.5 mg/kg for testing orally delivered DPP4 inhibitors and 1.2 mg/kg for testing intratracheally delivered DPP4 inhibitors) or PBS in sham group was intratracheally injection into mice lung at day 0. DPP4 inhibitors or vehicle control were given to mice starting from one day before LPS injection (day −1).

All animals were sacrificed at day 3.5 after LPS injection. Bronchoalveolar lavage fluid (BALF) was retrieved using standard method. 1 ml 4% formalin was used to inflate the lung, which was subsequently fixed in 4% formalin for 24 hours and preserved in 70% EtOH until histological process.

For readouts, total protein content in BALF was quantified using BCA assay: pulmonary inflammation and damage were assessed using H&E staining.

Experimental Methods of Bleomycin Model

Bleomycin (Hospira) was used to induce lung fibrosis in mice. Body weight matched (24 gram~28 gram) male C57BL/6J mice at 10-12 weeks of age were selected to use in bleomycin model.

For orally delivered DPP4 inhibitors. compounds were dissolved in PBS resulting in clear solution. Vehicle control or DPP4 inhibitors were dosed at 10 ml/kg through oral gavage once or twice a day selected based on PK profile. For intratracheally delivered DPP4 inhibitors, compounds were dissolved in PBS resulting in clear solution. Vehicle control or DPP4 inhibitors were dosed at 2 ml/kg through a 22 g flexible catheter every four days.

0.5 U/kg Bleomycin or PBS in sham group was intratracheally injection into mice lung at day 0. DPP4 inhibitors or vehicle control were given to mice starting from one day before bleomycin injection (day −1).

All animals were sacrificed at day 20 after bleomycin injection. Bronchoalveolar lavage fluid (BALF) was retrieved using standard method. 1 ml 4% formalin was used to inflate the lung, which was subsequently fixed in 4% formalin for 24 hours and preserved in 70% EtOH until histological process.

For readouts, body weight was measured every day; total protein content in BALF was quantified using BCA assay; pulmonary fibrosis was assessed using Masson's trichrome staining.

High oral doses of 3 approved gliptins (Sitagliptin, Saxagliptin, and Linagliptin) were found to be efficacious in mouse models of acute lung injury induced by LPS (body weight sparing, histological scoring, BALF protein, inflammatory resolution) as well as bleomycin-induced lung fibrosis (body weight sparing, histological scoring, collagen content, percent fibrotic area).

The three exemplary gliptins required doses multiple folds above the efficacious dose for efficacy in oral glucose tolerance test (OGTT) models. Dose projections indicate that these three exemplary gliptins would likely require about 10 times the human dose to achieve efficacy in patients (Table 6), a result supported by mouse pharmacokinetic data (see Example 4).

TABLE 6

Dose ranges of exemplary gliptins.

| Drug | Recommended Human Dose | Dose required in mouse ALI | Dose required in mouse bleomycin | Estimated human dose |
|---|---|---|---|---|
| Sitagliptin | 100 mg QD | 100 mg/kg BID (10-20x HED) | 100 mg/kg BID (10-20xHED) | 1,000-2,000 mg QD |
| Vildagliptin | 50 mg BID | Not yet evaluated | Not yet evaluated | N/A |
| Saxagliptin | 2.5 or 5 mg QD | 50 mg/kg BID (10-20x HED) | 50 mg/kg BID (10-20x HED) | 500 mg BID |
| Linagliptin | 5 mg QD | 1 mg/kg QD, 2 mg/kg toxic in model (2x HED) | >10 mg/kg qD (>20x HED) | 50-100 mg QD |
| Gemigliptin | 50 mg QD | | | |
| Anagliptin | 100 or 200 mg BID | | | |
| Teneligliptin | 20 mg QD | | | |
| Alogliptin | 25 mg QD | Not yet evaluated | Not yet evaluated | N/A |
| Trelagliptin | 100 mg QW | | | |
| Omarigliptin | 12.5 or 25 mg QW | | | |
| Evogliptin | 5 mg QD | | | |
| Gosogliptin | 20 mg QD | | | |
| Dutogliptin | 200 or 400 mg QD | Not yet evaluated | Not yet evaluated | Not yet evaluated |

Example 4: Safety and Pharmacokinetic Profiling of Approved Gliptins

A. Safety. Gliptins are generally safe and well tolerated medications. Relevant safety information from publicly available sources is compiled in Table 7.

TABLE 7

Dose, selectivity, and reported adverse events (AEs), depicting the general safety of approved and late-stage investigational gliptins.

| Drug | Recommend-ed Human Dose | Selec-tivity DPP8/9 | Adverse Events |
|---|---|---|---|
| Sitagliptin | 100 mg QD | >2,600/ >2,600 | 800 mg/day QTc signal 600 mg/day for 10 days: No AE; |
| Vildagliptin | 50 mg BID | >250/ ~100 | 600 mg/day for 10 days: oedema, increases in CPK, AST, CRP |
| Saxagliptin | 2.5 or 5 mg QD | 400/75 | 400 mg/day for 14 days: No AE >10 mg/day results in decreased lymphocyte count |
| Linagliptin | 5 mg QD | >10,000/ >10,000 | 600 mg single dose: No AE |
| Gemigliptin | 50 mg QD | >23,000/ >23,000 | 600 mg/day for 10 days: One case of increased heartbeat |
| Anagliptin | 100 or 200 mg BID | 20/20 | 200 mg BID: no AE |
| Teneliglip-tin | 20 mg QD | 100/100 | 160 mg/day cardiac safety warning |
| Alogliptin | 25 mg QD | >10,000/ >10,000 | 800 mg single dose or 400 mg/dayf or 14 days: No serious AE. |
| Trelagliptin | 100 mg QW | >25,000/ >25,000 | 200 mg qW: no AE |
| Omariglip-tin | 12.5 or 25 mg QW | >40,000/ >40,000 | Not publicly available |
| Evogliptin | 5 mg QD | >600/ >600 | Not publicly available |
| Gosogliptin | 20 mg QD | 700/>500 | Not publicly available |
| Dutogliptin | 200 or 400 mg QD | Not known | Not publicly available |

Figure 6:
FIG. 6. Pharmacokinetic profiling of four gliptins.

B. Pharmacokinetic profiling. The purpose of this example is to demonstrate the surprisingly high oral doses required for therapeutic lung exposure of gliptins. Thus, four of the five gliptins currently approved by the U.S. FDA were each administered to mice orally (100 mg/kg) or through intratracheal (IT) or oropharyngeal (OP) routes (20 mg/kg). Following administration, lung exposure of each gliptin tested was observed at early time points but dropped off quickly (FIG. 6).

With IT or OP dosing only one fifth of the oral doses were required to achieve similar lung exposure. However, high doses of gliptins or more frequent dosing regimen are required to achieve trough values above the $EC_{50}$ for AEC2 proliferation.

Figure 7:
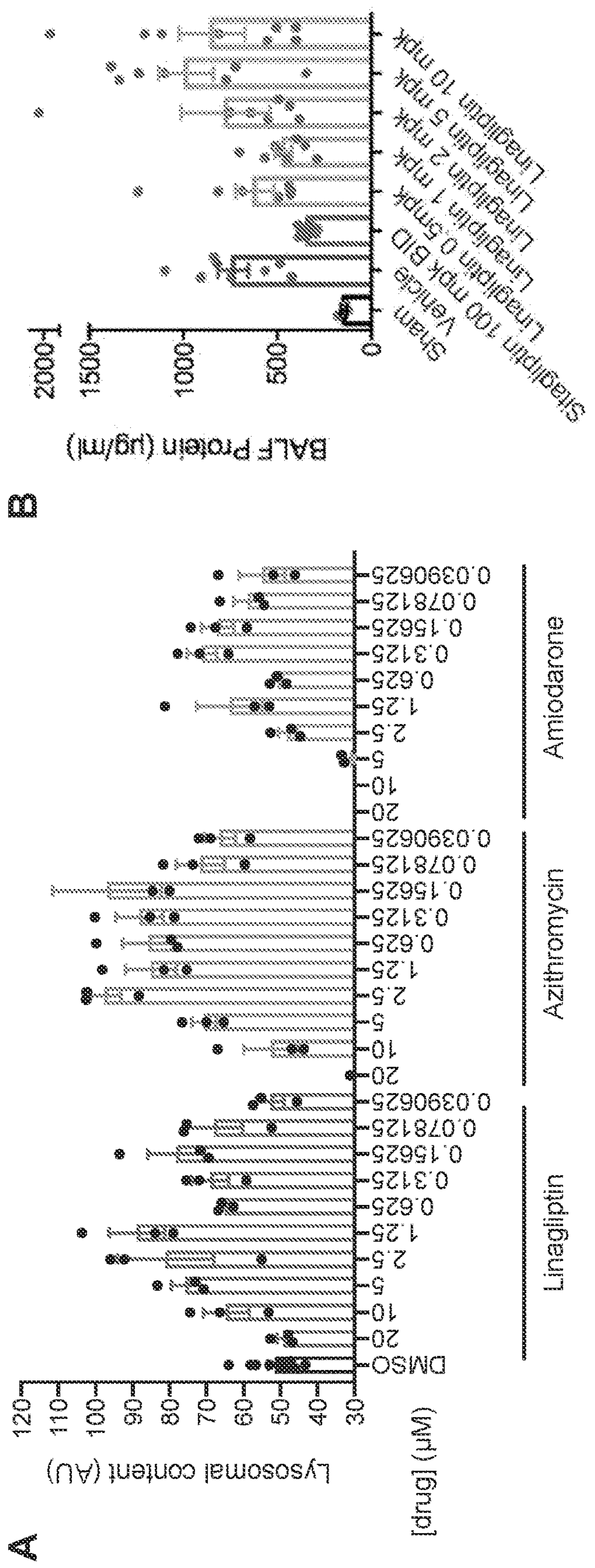
FIG. 7A and FIG. 7B.

Linagliptin displayed considerably higher lung exposure over the evaluated time frame. In contrast to its reported safety profile, Linagliptin displayed some unwanted effects, which may signal caution or preclude its direct oral administration at higher doses. Linagliptin exhibits excellent tissue exposure and a high volume of distribution because it is a cationic amphiphile. Consistent with this property, Linagliptin was found to induce significant phospholipidosis at low concentrations, similar to the positive controls used in the assays (FIG. 7A). Additionally, although Linagliptin is efficacious in animal models of lung disease, repeat dosing of Linagliptin was found to display a 'V-shaped' curve with minimal therapeutic index. Linagliptin is found to be efficacious at 1 mg/kg. but it displays antagonistic activity at doses 2 mg/kg or higher (FIG. 7B). These data indicate that while Linagliptin can be largely safe in inducing phospholipidosis in AEC2s. the gliptin could be of potential concern to an already at-risk IPF population.

Example 5. Unexpected Discovery of Dutogliptin Boronates Such as Compound (15) as a Prodrug Approach to Release Active Boronic Acid Dutogliptin in Lung Over Extended Period When Dosed Through Inhalation Like other gliptins. Dutogliptin (1) dosed IT in mice with PBS solution quickly cleared in lung (<24h. Table 8A). When its synthetic intermediate pinacol boronate (15) was dosed by IT route, the dutogliptin boronate (15) plasma and lung levels were very low and absent after 0.25 h (data not shown). The parent drug dutogliptin was detected in plasma and lung. The lung exposure was significantly higher than observed with IT dosing of dutogliptin itself (Table 8B). The drug was retained in the lung for over 48 h. The data clearly illustrated the unexpected lung retention ability of boronate prodrug 15.

TABLE 8A pharmacokinetics of dutogliptin (1) in mice with IT dosing
Individual and Mean Concentration of
dutogliptin (cpd 1) with 4.4 mg/kg IT dosing

| Time (h) | M1 + 3n | M2 + 3n | M3 + 3n | Mean | | SD | CV (%) |
|---|---|---|---|---|---|---|---|
| Plasma concentration (ng/mL) | | | | | | | |
| 0.250 | 9872 | 2394 | 8033 | 6766 | ± | 3897 | 57.6 |
| 3.00 | BQL | BQL | BQL | ND | ± | ND | ND |
| 7.00 | BQL | BQL | BQL | ND | ± | ND | ND |
| 24.0 | BQL | BQL | BQL | ND | ± | ND | ND |
| 48.0 | BQL | BQL | BQL | ND | ± | ND | ND |
| 96.0 | BQL | BQL | BQL | ND | ± | ND | ND |
| 168 | BQL | BQL | BQL | ND | ± | ND | ND |
| Bronchoalveolar lavage fluids concentration (ng/mL) | | | | | | | |
| 0.250 | 15446 | 49550 | 16744 | 27247 | ± | 19326 | 70.9 |
| 3.00 | 400 | 298 | 230 | 309 | ± | 85.6 | 27.7 |
| 7.00 | BQL | BQL | BQL | ND | ± | ND | ND |
| 24.0 | BQL | BQL | BQL | ND | ± | ND | ND |
| 48.0 | BQL | BQL | BQL | ND | ± | ND | ND |
| 96.0 | BQL | BQL | BQL | ND | ± | ND | ND |
| 168 | BQL | BQL | BQL | ND | ± | ND | ND |

TABLE 8A-continued pharmacokinetics of dutogliptin (1) in mice with IT dosing
Individual and Mean Concentration of
dutogliptin (cpd 1) with 4.4 mg/kg IT dosing

| Time (h) | M1 + 3n | M2 + 3n | M3 + 3n | Mean | | SD | CV (%) |
|---|---|---|---|---|---|---|---|
| Lung concentration (ng/g) | | | | | | | |
| 0.250 | 31521 | 65267 | 32729 | 43172 | ± | 19144 | 44.3 |
| 3.00 | 6797 | 5508 | 7333 | 6546 | ± | 938 | 14.3 |
| 7.00 | 3795 | 4914 | 4981 | 4563 | ± | 666 | 14.6 |
| 24.0 | 3717 | BQL | BQL | ND | ± | ND | ND |
| 48.0 | BQL | BQL | BQL | ND | ± | ND | ND |
| 96.0 | BQL | BQL | BQL | ND | ± | ND | ND |
| 168 | BQL | BQL | BQL | ND | ± | ND | ND |

TABLE 8B pharmacokinetics of dutogliptin boronate (15) in mice with IT dosing
Individual and Mean Concentration of dutogliptin with
1.8 mg/kg IT dosing of dutogliptin boronate (cpd 15)

| Time (h) | M1 + 3n | M2 + 3n | M3 + 3n | Mean | | SD | CV (%) |
|---|---|---|---|---|---|---|---|
| Plasma concentration (ng/mL) | | | | | | | |
| 0.250 | 31518 | 28671 | 59057 | 39749 | ± | 16782 | 42.2 |
| 3.00 | 836 | 654 | 574 | 688 | ± | 134 | 19.5 |
| 7.00 | BQL | BQL | BQL | ND | ± | ND | ND |
| 24.0 | BQL | BQL | BQL | ND | ± | ND | ND |
| 48.0 | BQL | BQL | BQL | ND | ± | ND | ND |
| 96.0 | BQL | BQL | BQL | ND | ± | ND | ND |
| 168 | BQL | BQL | BQL | ND | ± | ND | ND |
| Bronchoalveolar lavage fluids concentration (ng/mL) | | | | | | | |
| 0.250 | 21924 | 75878 | 95984 | 64595 | ± | 38297 | 59.3 |
| 3.00 | 2013 | 3480 | 5326 | 3606 | ± | 1660 | 46.0 |
| 7.00 | 896 | 593 | 1284 | 924 | ± | 346 | 37.5 |
| 24.0 | 480 | 430 | 477 | 462 | ± | 28.0 | 6.07 |
| 48.0 | 290 | BQL | BQL | ND | ± | ND | ND |
| 96.0 | BQL | BQL | BQL | ND | ± | ND | ND |
| 168 | BQL | BQL | BQL | ND | ± | ND | ND |
| Lung concentration (ng/g) | | | | | | | |
| 0.250 | 155155 | 156816 | 124742 | 145571 | ± | 18058 | 12.4 |
| 3.00 | 48558 | 27563 | 32802 | 36308 | ± | 10928 | 30.1 |
| 7.00 | 35088 | 26620 | 25968 | 29225 | ± | 5088 | 17.4 |
| 24.0 | 16368 | 17558 | 18817 | 17581 | ± | 1225 | 6.97 |
| 48.0 | 7681 | BQL | 6446 | 7064 | ± | ND | ND |
| 96.0 | BQL | BQL | BQL | ND | ± | ND | ND |
| 168 | BQL | BQL | BQL | ND | ± | ND | ND |

Figure 8:
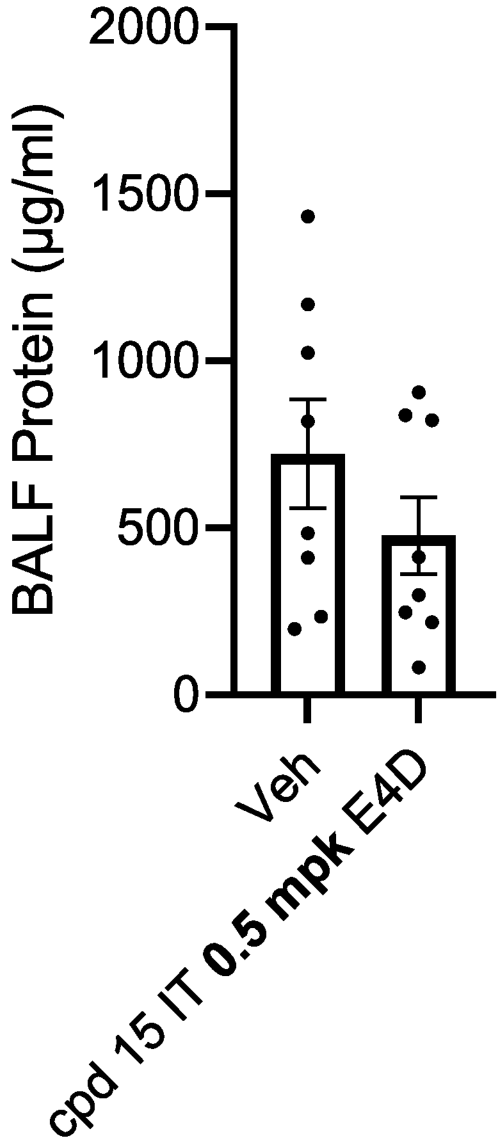
FIG. 8 Dutogliptin boronate (15) reduced BALF protein level when dosed 0.5 mg/kg once every four days through IT in a Bleomycin induced fibrosis model.

Based on the superior lung exposure, the dutogliptin boronate (15) was tested in Bleomycin-induced lung fibrosis mouse model When dosed at 0.5 mg/kg IT once every four days, the BALF protein level was reduced (FIG. 8).

We claim:

1. A method of selectively increasing the proliferation of cuboidal alveolar type 2 (AEC2) cells or restoring diminished proliferation of AEC2 cells, which comprises administering to a subject in need thereof an effective amount of a dipeptidyl peptidase-4(DPP4) inhibitor.

2. The method of claim 1, wherein the DPP4 inhibitor is:

((R)-1-(((R)-pyrrolidin-3-yl glycyl) pyrrolidin-2-yl)boronic acid (Dutogliptin);

ethyl 4-((2-((2S,4S)-2-cyano-4-fluoropyrrolidin-1-yl)-2-oxoethyl)amino)bicyclo [2.2.2]octane-1-carboxylate (Bisegliptin);

(1S,3S,5S)-2-((2S)-2-amino-2-((1S,3R,5S)-3-hydroxy-adamantan-1-yl)acetyl)-2-azabicyclo[3.1.0]hexane-3-carbonitrile (saxagliptin);

methyl (R)-7-(3-amino-4-(2,4,5-trifluorophenyl)butanoyl)-3-(trifluoromethyl)-5,6,7,8-tetrahydroimidazo [1,5-a]pyrazine-1-carboxylate (Retagliptin);

(R)-2-((6-(3-aminopiperidin-1-yl)-3-methyl-2,4-dioxo-3,4-dihydropyrimidin-1 (2H) -yl)methyl benzonitrile (alogliptin);

((2S,4S)-4-(4-(3-methyl-1-phenyl-1H-pyrazol-5-yl)piperazin-1-yl)pyrrolidin-2-yl)(thiazolidin-3-yl)methanone (Teneligliptin);

(2R,3S,5R)-2-(2,5-difluorophenyl)-5-(2-(methylsulfonyl)-2,6-dihydropyrrolo [3,4-c]pyrazol -5(4H)-yl)tetrahydro-2H-pyran-3-amine (omarigliptin);

(R)-2-((6-(3-aminopiperidin-1-yl)-3-methyl-2,4-dioxo-3,4-dihydropyrimidin-1 (2H) -yl)methyl)-4-fluorobenzonitrile (Trelagliptin);

(S)-N-(2-((2-(2-cyanopyrrolidin-1-yl)-2-oxoethyl) amino)-2-methylpropyl)-2-methylpyrazolo [1,5-a]pyrimidine-6-carboxamide (Anagliptin);

(R)-4-((R)-3-amino-4-(2,4,5-trifluorophenyl)butanoyl)-3-(tert-butoxymethyl)piperazin-2-one (evogliptin);

((2S,4S)-4-(4-(pyrimidin-2-yl)piperazin-1-yl)pyrrolidin-2-yl)(pyrrolidin-1-yl) methanone;

(R)-2-((7-(3-aminopiperidin-1-yl)-3,5-dimethyl-2-oxo-2,3-dihydro-1H-imidazo [4,5-b]pyridin-1-yl)methyl) benzonitrile dichloride (Imigliptin dihydrochloride);

(2S,4S)-1-((S)-2-amino-3,3-bis(4-fluorophenyl)propanoyl)-4-fluoropyrrolidine-2-carbonitrile (Denagliptin);

(2S,4S)-1-(((1R,3S)-3-((1H-1,2,4-triazol-1-yl)methyl)cyclopentyl)glycyl)-4-fluoropyrrolidine-2-carbonitrile (Melogliptin);

5-((S)-2-((2-((S)-2-cyanopyrrolidin-1-yl)-2-oxoethyl) amino)propyl)-N2,N2,N8,N8-tetramethyl-5-(1H-tetrazol-5-yl)-10,11-dihydro-5H-dibenzo[a,d][7]annulene-2,8-dicarboxamide (AMG-222);

(2S,4S)-4-fluoro-1-((1-hydroxy-2-methylpropan-2-yl) glycyl)pyrrolidine-2-carbonitrile;

ethyl 4-((2-((2S,4S)-2-cyano-4-fluoropyrrolidin-1-yl)-2-oxoethyl)amino)bicyclo[2.2.2]octane-1-carboxylate (KRP-104);

((R)-1-((S)-2-aminopropanethioyl)pyrrolidin-2-yl)boronic acid (ARI-2243);

(R)-2-((3-(3-aminopiperidin-1-yl)-6-methyl-5-oxo-1,2,4-triazin-4 (5H)-yl)methyl)-4fluorobenzonitrile (Fotagliptin);

(3aR,5s,6aS)-5-((2-((2S,4S)-2-cyano-4-fluoropyrrolidin-1-yl)-2-oxoethyl) amino)-N,N,5-trimethylhexahydrocyclopenta[c]pyrrole-2 (1H)-carboxamide (SHR-117887);

3-(but-2-yn-1-yl)-5-methyl-2-(piperazin-1-yl)-3,5-dihydro-4H-imidazo[4,5-d] pyridazin-4-one;

(S)-8-(3-aminopiperidin-1-yl)-7-(but-2-yn-1-yl)-1-((5-fluorobenzo[d]thiazol-2-yl)methyl)-3-methyl-3,7-dihydro-1H-purine-2,6-dione (Yogliptin);

(S)-1-((2S,3S,11bS)-2-amino-9,10-dimethoxy-1,3,4,6,7,11b-hexahydro-2H-pyrido [2,1-alisoquinolin-3-yl)-4-(fluoromethyl)pyrrolidin-2-one (DPP-728/carmegliptin));

(2S,3S)-2-amino-3-methyl-1-(thiazolidin-3-yl)pentan-1-one (P32/98);

8-((3R)-3-aminocyclohexyl)-1-((7-fluorobenzo[c][1,2,5] thiadiazol-5-yl)methyl)-3-methyl-7-(prop-2-yn-1-yl)-3,7-dihydro-1H-purine-2.6-dione (TQ-F3083);

(2R,3S,5R)-2-(2,5-difluorophenyl)-5-(5-(methylsulfonyl)-3,4,5,6-tetrahydropyrrolo [3,4-c]pyrrol-2 (1H)-yl) tetrahydro-2H-pyran-3-amine (ZYDPLA-1);

DSP-7238;

2-(4-((2-((2S,5R)-2-cyano-5-ethynylpyrrolidin-1-yl)-2-oxoethyl)amino)-4-methylpiperidin-1-yl)isonicotinic acid (ABT-279);

((R)-1-(L-valyl)pyrrolidin-2-yl)boronic acid (BXCL-701/talabostat));

2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl)ethan-1-one (compound 15);

4-((2-((2S,4S)-2-cyano-4-fluoropyrrolidin-1-yl)-2-oxoethyl)amino)bicyclo[2.2.2] octane-1-carboxylic acid;

methyl 4-((2-((2S,4S)-2-cyano-4-fluoropyrrolidin-1-yl)-2-oxoethyl) amino)bicyclo[2.2.2] octane-1-carboxylate;

(2S)-1-(((1S,3R,5R)-3-aminoadamantan-1-yl)glycyl)pyrrolidine-2-carbonitrile;

(2S)-1-(((1r,3R,5S)-adamantan-1-yl)glycyl)pyrrolidine-2-carbonitrile;

(R)-2-((8-(3-aminopiperidin-1-yl)-7-(but-2-yn-1-yl)-3-methyl-2,6-dioxo-2,3,6,7-tetrahydro -1H-purin-1-yl) methyl)-5-chlorobenzoic acid;

methyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate;

(R)-2- ((4-(3-aminopiperidin-1-yl)-3-(but-2-yn-1-yl)-2,6-dioxo-3,6-dihydropyrimidin-1 (2H) -yl) methyl)-6-fluorobenzoic acid;

methyl (R)-2-((4-(3-aminopiperidin-1-yl)-3-(but-2-yn-1-yl)-2,6-dioxo-3,6-dihydropyrimidin -1 (2H)-yl) methyl)-6-fluorobenzoate;

(R)-3-((4-(3-aminopiperidin-1-yl)-3-(but-2-yn-1-yl)-2,6-dioxo-3,6-dihydropyrimidin-1 (2H) -yl)methyl) benzoic acid;

methyl (R)-3-((4-(3-aminopiperidin-1-yl)-3-(but-2-yn-1-yl)-2,6-dioxo-3,6-dihydropyrimidin -1 (2H)-yl)methyl) benzoate;

(R)-7-(3-amino-4-(2,4,5-trifluorophenyl)butanoyl)-3-(trifluoromethyl)-5,6,7,8-tetrahydroimidazo[1,5-a]pyrazine-1-carboxylic acid;

(R)-3-amino-1-((R)-2-benzylpiperazin-1-yl)-4-(2-fluorophenyl)butan-1-one;

(7R)-4-((R)-3-amino-4-(2,4,5-trifluorophenyl)butanoyl)-7-methyl-3-(pyridin-2-ylmethyl)-1,4-diazepan-2-one;

(3R,7R)-4-((R)-3-amino-4-(2,4,5-trifluorophenyl)butanoyl)-7-methyl-3-(pyridin-2-ylmethyl) -1,4-diazepan-2-one;

(R)-4-((R)-3-amino-4-(2,5-difluorophenyl) butanoyl)-1-ethyl-3-methyl-1,4-diazepan-2-one;

(R)-3-amino-4-(3,4-difluorophenyl)-1-(piperazin-1-yl) butan-1-one;

or a pharmaceutically acceptable salt thereof.

3. The method of claim 2, wherein the DPP4 inhibitor is:

((R)-1-(((R)-pyrrolidin-3-yl)glycyl)pyrrolidin-2-yl)boronic acid (Dutogliptin);

ethyl 4-((2-((2S,4S)-2-cyano-4-fluoropyrrolidin-1-yl)-2-oxoethyl)amino)bicyclo[2.2.2] octane-1-carboxylate (Bisegliptin);

(1S,3S,5S)-2-((2S)-2-amino-2-((1S,3R,5S)-3-hydroxyadamantan-1-yl) acetyl)-2- azabicyclo[3.1.0] hexane-3-carbonitrile (saxagliptin);

methyl (R)-7-(3-amino-4-(2,4,5-trifluorophenyl) butanoyl)-3-(trifluoromethyl)-5,6,7,8-tetrahydroimidazo[1,5-a]pyrazine-1-carboxylate (Retagliptin);

(R)-2-((6-(3-aminopiperidin-1-yl)-3-methyl-2,4-dioxo-3,4-dihydropyrimidin-1 (2H) -yl)methyl)benzonitrile (alogliptin);

Teneligliptin;
omarigliptin;
Trelagliptin;
Anagliptin;
evogliptin;
((2S,4S)-4-(4-(pyrimidin-2-yl)piperazin-1-yl)pyrrolidin-2-yl)(pyrrolidin-1-yl)methanone;
or a pharmaceutically acceptable salt thereof.

4. The method of claim 2, wherein the DPP4 inhibitor is:
Imigliptin dihydrochloride;
Denagliptin;
Melogliptin;
AMG-222;
(2S.4S)-4-fluoro-1-((1-hydroxy-2-methylpropan-2-yl)glycyl)pyrrolidine-2-carbonitrile;
KRP-104;
ARI-2243;
Fotagliptin;
SHR-117887;
3-(but-2-yn-1-yl)-5-methyl-2-(piperazin-1-yl)-3,5-dihydro-4H-imidazo[4,5-d] pyridazin-4-oneE;
Yogliptin;
DPP-728 (carmegliptin);
(2S,3S)-2-amino-3-methyl-1-(thiazolidin-3-yl)pentan-1-one (P32/98);
8-((3R)-3-aminocyclohexyl)-1-((7-fluorobenzo[c] [1.2.5] thiadiazol-5-yl)methyl)-3-methyl-7-(prop-2-yn-1-yl)-3,7-dihydro-1H-purine-2.6-dione (TQ-F3083);
(2R,3S,5R)-2-(2,5-difluorophenyl)-5-(5-(methylsulfonyl)-3,4,5,6-tetrahydropyrrolo [3,4-c]pyrrol-2 (1H)-yl) tetrahydro-2H-pyran-3-amine (ZYDPLA-1);
DSP-7238;
2-(4-((2-((2S,5R)-2-cyano-5-ethynylpyrrolidin-1-yl)-2-oxoethyl)amino)-4-methylpiperidin-1-yl)isonicotinic acid (ABT-279);
((R)-1-(L-valyl)pyrrolidin-2-yl)boronic acid (BXCL-701/talabostat));
or a pharmaceutically acceptable salt thereof.

5. The method of claim 2, wherein the DPP4 inhibitor is:
2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl)ethan-1-one (compound 15);
4-((2-((2S,4S)-2-cyano-4-fluoropyrrolidin-1-yl)-2-oxoethyl)amino)bicyclo[2.2.2] octane-1-carboxylic acid;
methyl 4-((2-((2S,4S)-2-cyano-4-fluoropyrrolidin-1-yl)-2-oxoethyl)amino)bicyclo[2.2.2] octane-1-carboxylate;
(2S)-1-(((1S,3R,5R)-3-aminoadamantan-1-yl)glycyl)pyrrolidine-2-carbonitrile;
(2S)-1-(((1r,3R,5S)-adamantan-1-yl)glycyl)pyrrolidine-2-carbonitrile;
(R)-2-((8-(3-aminopiperidin-1-yl)-7-(but-2-yn-1-yl)-3-methyl-2,6-dioxo-2,3,6,7-tetrahydro -1H-purin-1-yl) methyl)-5-chlorobenzoic acid;
methyl (R)-2-((8-(3-aminopiperidin-1-yl)-7-(but-2-yn-1-yl)-3-methyl-2,6-dioxo-2,3,6,7-tetrahydro-1H-purin-1-yl) methyl)-5-chlorobenzoate;
(R)-2-((4-(3-aminopiperidin-1-yl)-3-(but-2-yn-1-yl)-2,6-dioxo-3,6-dihydropyrimidin-1 (2H) -yl) methyl)-6-fluorobenzoic acid;
methyl (R)-2-((4-(3-aminopiperidin-1-yl)-3-(but-2-yn-1-yl)-2,6-dioxo-3,6-dihydropyrimidin -1 (2H)-yl) methyl)-6-fluorobenzoate;
(R)-3-((4-(3-aminopiperidin-1-yl)-3-(but-2-yn-1-yl)-2,6-dioxo-3,6-dihydropyrimidin-1 (2H) -yl) methyl) benzoic acid;
methyl (R)-3-((4-(3-aminopiperidin-1-yl)-3-(but-2-yn-1-yl)-2,6-dioxo-3,6-dihydropyrimidin -1 (2H)-yl) methyl) benzoate;
(R)-7-(3-amino-4-(2,4,5-trifluorophenyl) butanoyl)-3-(trifluoromethyl)-5,6,7,8-tetrahydroimidazo[1,5-a] pyrazine-1-carboxylic acid;
(R)-3-amino-1-((R)-2-benzylpiperazin-1-yl)-4-(2-fluorophenyl) butan-1-one;
(7R)-4-((R)-3-amino-4-(2,4,5-trifluorophenyl) butanoyl)-7-methyl-3-(pyridin-2-ylmethyl)-1,4-diazepan-2-one;
(3R,7R)-4-((R)-3-amino-4-(2,4,5-trifluorophenyl) butanoyl)-7-methyl-3-(pyridin-2-ylmethyl)- 1,4-diazepan-2-one;
(R)-4-((R)-3-amino-4-(2,5-difluorophenyl)butanoyl)-1-ethyl-3-methyl-1,4-diazepan-2-one;
(R)-3-amino-4-(3,4-difluorophenyl)-1-(piperazin-1-yl) butan-1-one;
or a pharmaceutically acceptable salt thereof.

6. The method of claim 2, wherein the DPP4 inhibitor is:
((R)-1-(((R)-pyrrolidin-3-yl)glycyl)pyrrolidin-2-yl)boronic acid (Dutogliptin);
ethyl 4-((2-((2S,4S)-2-cyano-4-fluoropyrrolidin-1-yl)-2-oxoethyl)amino) bicyclo[2.2.2] octane-1-carboxylate (Bisegliptin); '(1S,3S,5S)-2-((2S)-2-amino-2-((1S,3R,5S)-3-hydroxyadamantan-1-yl) acetyl)-2-azabicyclo [3.1.0]hexane-3-carbonitrile (saxagliptin);
methyl(R)-7-(3-amino-4-(2,4,5-trifluorophenyl)butanoyl)-3-(trifluoromethyl)-5,6,7,8-tetrahydroimidazo [1,5-a]pyrazine-1-carboxylate (Retagliptin);
(R)-2-((6-(3-aminopiperidin-1-yl)-3-methyl-2,4-dioxo-3,4-dihydropyrimidin-1 (2H) -yl) methyl) benzonitrile (alogliptin);
Teneligliptin;
omarigliptin;
Trelagliptin;
Anagliptin;
evogliptin;
((2S.4S)-4-(4-(pyrimidin-2-yl) piperazin-1-yl) pyrrolidin-2-yl) (pyrrolidin-1-yl) methanone;
2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl ethan-1-one (compound 15);
4-((2-((2S,4S)-2-cyano-4-fluoropyrrolidin-1-yl)-2-oxoethyl)amino)bicyclo[2.2.2] octane-1-carboxylic acid;
methyl 4-((2-((2S,4S)-2-cyano-4-fluoropyrrolidin-1-yl)-2-oxoethyl) amino)bicyclo[2.2.2] octane-1-carboxylate;
(2S)-1-(((1S,3R,5R)-3-aminoadamantan-1-yl)glycyl)pyrrolidine-2-carbonitrile;
(2S)-1-(((1r,3R,5S)-adamantan-1-yl)glycyl)pyrrolidine-2-carbonitrile;
(R)-2-((8-(3-aminopiperidin-1-yl)-7-(but-2-yn-1-yl)-3-methyl-2,6-dioxo-2,3,6,7-tetrahydro -1H-purin-1-yl) methyl)-5-chlorobenzoic acid;
methyl(R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate;
(R)-2-((4-(3-aminopiperidin-1-yl)-3-(but-2-yn-1-yl)-2,6-dioxo-3,6-dihydropyrimidin-1 (2H) -yl) methyl)-6-fluorobenzoic acid;
methyl (R)-2-((4-(3-aminopiperidin-1-yl)-3-(but-2-yn-1-yl)-2,6-dioxo-3,6-dihydropyrimidin -1 (2H)-yl) methyl)-6-fluorobenzoate;
(R)-3-((4-(3-aminopiperidin-1-yl)-3-(but-2-yn-1-yl)-2,6-dioxo-3,6-dihydropyrimidin-1 (2H)- yl) methyl) benzoic acid;

methyl (R)-3-((4-(3-aminopiperidin-1-yl)-3-(but-2-yn-1-yl)-2,6-dioxo-3,6-dihydropyrimidin- 1 (2H)-yl)methyl) benzoate;

(R)-7-(3-amino-4-(2,4,5-trifluorophenyl)butanoyl)-3-(trifluoromethyl)-5,6,7,8-tetrahydroimidazo[1,5-a]pyrazine-1-carboxylic acid;

(R)-3-amino-1-((R)-2-benzylpiperazin-1-yl)-4-(2-fluorophenyl) butan-1-one;

(7R)-4-((R)-3-amino-4-(2,4,5-trifluorophenyl) butanoyl)-7-methyl-3-(pyridin-2-ylmethyl)-1,4-diazepan-2-one;

(3R,7R)-4-((R)-3-amino-4-(2,4,5-trifluorophenyl) butanoyl)-7-methyl-3-(pyridin-2-ylmethyl) -1,4-diazepan-2-one;

(R)-4-((R)-3-amino-4-(2,5-difluorophenyl)butanoyl)-1-ethyl-3-methyl-1,4-diazepan-2-one;

(R)-3-amino-4-(3,4-difluorophenyl)-1-(piperazin-1-yl) butan-1-one;

or a pharmaceutically acceptable salt thereof.

7. The method of claim 2, wherein the DPP4 inhibitor is 2-(((R)-pyrrolidin-3-yl)amino)-1-((R)-2-((3aS,4S,6S,7aR)-3a,5,5-trimethylhexahydro-4,6-methanobenzo[d][1,3,2]dioxaborol-2-yl)pyrrolidin-1-yl)ethan-1-one (compound 15) or a pharmaceutically acceptable salt thereof.

8. The method of claim 2, wherein the DPP4 inhibitor is saxagliptin or a pharmaceutically acceptable salt thereof.

9. The method of claim 8, wherein the DPP4 inhibitor is administered to the subject in an amount of about 500 mg BID.

10. The method of claim 1, wherein the DPP4 inhibitor is administered to the lungs of the subject.

11. The method of claim 9, wherein the DPP4 inhibitor is administered by inhalation.

12. The method of claim 1, wherein the patient suffers from epithelial degeneration or maladaptive remodeling.

* * * * *